(12) United States Patent
Powers et al.

(10) Patent No.: US 6,635,741 B1
(45) Date of Patent: Oct. 21, 2003

(54) G-PROTEIN COUPLED RECEPTOR BCA-GPCR-3

(75) Inventors: Scott Powers, Greenlawn, NY (US); Jianxin Yang, Commack, NY (US); Gene Cutler, San Francisco, CA (US)

(73) Assignee: Tularik Inc., South San Francisco, CA (US)

( * ) Notice: Subject to any disclaimer, the term of this patent is extended or adjusted under 35 U.S.C. 154(b) by 0 days.

(21) Appl. No.: 09/546,986

(22) Filed: Apr. 11, 2000

Related U.S. Application Data

(63) Continuation-in-part of application No. 09/524,730, filed on Mar. 14, 2000.

(51) Int. Cl.⁷ ...................... C07K 14/705; C12N 15/12
(52) U.S. Cl. ...................... 530/350; 435/69.5; 435/71.1; 435/71.2; 435/325; 435/320.1; 435/252.3; 435/254.11; 435/471; 536/23.5
(58) Field of Search .................. 530/350; 435/69.1, 435/71.1, 71.2, 325, 320.1, 252.3, 254.11, 471; 536/23.1, 24.3, 24.31, 23.5

(56) References Cited

FOREIGN PATENT DOCUMENTS

| WO | WO 96/30406 A1 | 10/1996 |
| WO | WO 01/27158 A2 | 4/2001 |
| WO | WO 01/68805 A2 | 9/2001 |

OTHER PUBLICATIONS

Buck, et al. "A Novel Multigene Family May Encode Odorant Receptors: A Molecular Basis for Odor Recognition"; *Cell*, vol. 65, 175–187, Apr., 1991.

Birren, B. et al. "Homo sapiens chromosome 18, clone RP11–482N10" Database Genembl (Online) Accession AC023386, nucleotides 98850–993300 and nucleotides 75400–76070.

Buck, et al. "A Novel Multigene Family May Encode Odorant Receptors: A Molecular Basis for Odor Recognition" *Cell* (Apr. 1991) vol. 65, pp. 175–187.

Carmeci, et al. "Identification of a Gene (GPR30) with Homology to the G–Protein–Coupled Receptor Superfamily Associated with Estrogen Receptor Expression in Breast Cancer" *Genomics* (Nov. 1997) vol. 45(3).

Drutel, G. et al. "Cloning of OL1, A Putative Olfactory Receptor and Its Expression in the Developing Rat Heart" *Receptors and Channels* (1995) Vo. 3, pp. 33–40.

Mikayama, et al. "Molecular Cloning and Functional Expression of a cDNA Encoding Glycosylation–inhibition Factor" *Proc. Natl. Acad.Sci USA* (Nov. 1993) vol. 90, pp. 10056–10060.

Nef, et al. "Spatial Pattern of Receptor Expression in the Olfactory Epithelium" *Proc. of Nat. Acad. Sci. USA* (Oct. 1992, vol. 89; pp. 8948–8952.

Voet, et al. "Sickle–Cell Anemia: The Influence of Natural Selection" *Biochemistry*, 10th Ed. published by John Wiley & Sons, Inc. (1990), pp. 228–234.

*Primary Examiner*—Prema Mertz
(74) *Attorney, Agent, or Firm*—Townsend and Townsend and Crew LLP

(57) ABSTRACT

The invention provides isolated nucleic acid and amino acid sequences of four novel G-protein coupled receptors that are amplified in breast cancer cells, antibodies to such receptors, methods of detecting such nucleic acids and receptors, and methods of screening for modulators of G-protein coupled receptors.

4 Claims, 3 Drawing Sheets

| SAMPLE | | DNA COPY |
|---|---|---|
| DUKE BREAST TUMORS | | GPCR3 |
| d47 | 90-325 | 10.2 |
| d45 | 90-183 | 8.2 |
| d99 | 96-194 | 7.8 |
| d152 | 93-627 | 7 |
| d164 | 90-282 | 7 |
| d88 | 89-173 | 6.6 |
| d25 | 88-595 | 5.9 |
| d140 | 89-892 | 5 |
| d113 | 95-246 | 5 |
| d39 | 89-754 | 4.7 |
| d27 | 88-647 | 4.4 |
| d58 | 90-864 | 3.7 |
| d80 | 94-804 | 2.7 |
| FREQUENCY | | 15% |
| BREAST CANCER CELL LINES | | |
| bre1 | ala 8 | 2.2 |
| bre3 | BT474 | 3.4 |
| bre25 | MDA-MB-453 | 3 |
| bre31 | ZR-75-1 | 6.3 |
| FREQUENCY | | 14% |
| | | |

*FIG. 1.*

2 RT-QPCR DATA

| SAMPLE | GENE EXPRESSION | GENOMIC AMPLIFICATION |
|---|---|---|
| Me* | 1 | 1 |
| BT483 | 2.5 | 1 |
| ZR-75-30 | 3 | 1 |
| SK-BR3 | 6 | 1 |
| BT474 | 3 | 3 |
| MDA-MD453 | 5 | 3 |
| ZR-75-1 | 9 | 6 |
| MG* | 1 | 1 |
| 91-845 | 7 | 5 |

* NORMAL MAMMARY EPITHELIAL CELL (ME) AND NORMAL MAMMARY GLAND TISSUE (MG)

*FIG. 3.*

G-PROTEIN COUPLED RECEPTOR BCA-GPCR-3

CROSS-REFERENCES TO RELATED APPLICATIONS

This application claims the benefit of U.S. Ser. No. 09/524,730, filed Mar. 14, 2000, herein incorporated by reference in its entirety.

STATEMENT AS TO RIGHTS TO INVENTIONS MADE UNDER FEDERALLY SPONSORED RESEARCH AND DEVELOPMENT

Not applicable.

FIELD OF THE INVENTION

The invention provides isolated nucleic acid and amino acid sequences of four novel G-protein coupled receptors that are amplified in breast cancer cells, antibodies to such receptors, methods of detecting such nucleic acids and receptors, and methods of screening for modulators of G-protein coupled receptors.

BACKGROUND OF THE INVENTION

G-protein coupled receptors are cell surface receptors that indirectly transduce extracellular signals to downstream effectors, which can be intracellular signaling proteins, enzymes, or channels, and changes in the activity of these effectors then mediate subsequent cellular events. The interaction between the receptor and the downstream effector is mediated by a G-protein, a heterotrimeric protein that binds GTP. G-protein coupled receptors ("GPCRs") typically have seven transmembrane regions, along with an extracellular domain and a cytoplasmic tail at the C-terminus. These receptors form a large superfamily of related receptors molecules that play a key role in many signaling processes, such as sensory and hormonal signal transduction. For example, a large family of olfactory GPCRs has been identified (see, e.g., Buck & Axel, *Cell* 65:175–187 (1991)). The further identification of GPCRs is important for understanding the normal process of signal transduction and as well as its involvement in pathologic processes. For example, GPCRs can be used for disease diagnosis as well as for drug discovery. Further identification of novel GPCRs is therefore of great interest.

SUMMARY OF THE INVENTION

The present invention thus provides for the first time four novel nucleic acids encoding G protein coupled receptors that are amplified and or overexpressed in breast cancer cells. These nucleic acids and the polypeptides that they encode are referred to as "breast cancer amplified G-protein coupled receptors" or "BCA-GPCRs," i.e., "BCA-GPCR-1," "BCA-GPCR-2," "BCA-GPCR-3," and "BCA-GPCR-4." These BCA-GPCRs are components of signal transduction pathways in cells, and can be used for diagnosis of cancer, in particular breast cancers, as well as in screening assays for therapeutic compounds, e.g., for the treatment of cancer. For example, antibodies to and antagonists of BCA-GPCR-3 can be used as cancer therapeutics.

In one aspect, the present invention provides an isolated nucleic acid encoding a G-protein coupled receptor polypeptide, the polypeptide encoded by the nucleic acid comprising greater than 70% amino acid identity to an amino acid sequence of SEQ ID NO:2, SEQ ID NO:4, SEQ ID NO:6, or SEQ ID NO:8.

In another aspect, the present invention provides an isolated nucleic acid encoding a G-protein coupled receptor polypeptide, wherein the nucleic acid specifically hybridizes under stringent hybridization conditions to a nucleic acid having a nucleotide sequence of SEQ ID NO:1, SEQ ID NO:3, SEQ ID NO:5, or SEQ ID NO:7.

In another aspect, the present invention provides an isolated nucleic acid encoding a G-protein coupled receptor polypeptide, the polypeptide encoded by the nucleic acid comprising greater than about 70% amino acid identity to a polypeptide having an amino acid sequence of SEQ ID NO:2, SEQ ID NO:4, SEQ ID NO:6 or SEQ ID NO:8, wherein the nucleic acid selectively hybridizes under moderately stringent hybridization conditions to a nucleotide sequence of SEQ ID NO:1, SEQ ID NO:3, SEQ ID NO:5, or SEQ ID NO:7.

In another aspect, the present invention provides an expression vector comprising an isolated nucleic acid encoding a G-protein coupled receptor of the invention, and a host cell comprising the expression vector.

In one embodiment, the nucleic acid comprises a nucleotide sequence of SEQ ID NO:1, SEQ ID NO:3, SEQ ID NO:5, or SEQ ID NO:7. In another embodiment, the nucleic acid is from a human, a mouse, or a rat. In another embodiment, the nucleic acid is amplified by primers that specifically hybridize under stringent hybridization conditions to the same sequence as primer sets selected from the group consisting of:

ATGTTGGGGAACGTCGCCATC (SEQ ID NO:9) and
TCATCCACAGAGCCTCCAGAT (SEQ ID NO:10);

ATGGGAAAGGACAATCCAGTT (SEQ ID NO:11) and
CTAAGAGAGTAACTCCAGCAA (SEQ ID NO:12);

ATGGAAATAGCCAATGTGAGTTC (SEQ ID NO:13) and
TAAATTTGCGCCAGCTTGCCTG (SEQ ID NO:14); and ATGGTGAGACATACCAATGAGAG (SEQ ID NO:15) and
CATAAAATATTTACTCCCAGAGCC (SEQ ID NO:16).

In another aspect, the present invention provides an isolated G-protein coupled receptor polypeptide, the polypeptide comprising greater than about 70% amino acid sequence identity to an amino acid sequence of SEQ ID NO:2, SEQ ID NO:4, SEQ ID NO:6, or SEQ ID NO:8.

In one embodiment, the polypeptide specifically binds to polyclonal antibodies generated against SEQ ID NO:2, SEQ ID NO:4, SEQ ID NO:6 or SEQ ID NO:8, or an immunogenic portion thereof. In another embodiment, the polypeptide is from a human, a rat, or a mouse. In another embodiment, the polypeptide has an amino acid sequence of SEQ ID NO:2, SEQ ID NO:4, SEQ ID NO:6 or SEQ ID NO:8, or an immunogenic portion thereof.

In one embodiment, the polypeptide has G-protein coupled receptor activity.

In another aspect, the invention provides an antibody that binds to an isolated G-protein coupled receptor polypeptide, the polypeptide comprising greater than about 70% amino acid sequence identity to an amino acid sequence of SEQ ID NO:2, SEQ ID NO:4, SEQ ID NO:6, or SEQ ID NO:8.

In another aspect, the present invention provides a method for identifying a compound that modulates signal transduction of a BCA-PCR, the method comprising the steps of: (i) contacting the compound with a polypeptide comprising greater than 70% amino acid sequence identity to the amino acid sequence of SEQ ID NO:2, SEQ ID NO:4, SEQ ID NO:6, or SEQ ID NO:8; and (ii) determining the functional effect of the compound upon the polypeptide.

In one embodiment, the polypeptide is linked to a solid phase. In another embodiment, the polypeptide is covalently linked to a solid phase.

In one embodiment, the functional effect is determined by measuring changes in intracellular cAMP, IP3, or $Ca^{2+}$. In another embodiment, the functional effect is a chemical effect or a physical effect. In another embodiment, the functional effect is determined by measuring binding of the compound to the polypeptide.

In one embodiment, the polypeptide is recombinant. In another embodiment, the polypeptide is expressed in a cell or cell membrane, e.g., a eukaryotic cell or cell membrane.

In another aspect, the present invention provides a method of treating cancer, the method comprising the step of contacting a cancer cell with a therapeutically effective amount of a compound identified using the methods described above.

In one embodiment, the cancer is breast cancer.

In another embodiment, the compound is an antagonist of a polypeptide, the polypeptide comprising greater than 70% amino acid identity to the amino acid sequence of SEQ ID NO:6.

In another aspect, the present invention provides a method of treating cancer, the method comprising the steps of contacting a cancer cell with a therapeutically effective amount of an antibody, the antibody specifically binding to a polypeptide comprising greater than 70% amino acid identity to the amino acid sequence of SEQ ID NO:2, SEQ ID NO:4, SEQ ID NO:6, or SEQ ID NO:8.

In one embodiment, the antibody specifically binds to a polypeptide comprising greater than 70% amino acid identity to the amino acid sequence of SEQ ID NO:6.

In another aspect, the present invention provides a method of detecting the presence of an BCA-GPCR nucleic acid or polypeptide in human tissue, the method comprising the steps of: (i) isolating a biological sample; (ii) contacting the biological sample with a BCA-GPCR-specific reagent that selectively associates with an BCA-GPCR nucleic acid or polypeptide; and, (iii) detecting the level of BCA-GPCR-specific reagent that selectively associates with the sample.

In one embodiment, the BCA-GPCR-specific reagent is selected from the group consisting of: BCA-GPCR-specific antibodies, BCA-GPCR-specific oligonucleotide primers, and BCA-GPCR-specific nucleic acid probes.

In another embodiment, the tissue is breast cancer tissue.

In another aspect, the present invention provides a method of making a G-protein coupled receptor polypeptide, the method comprising the step of expressing the polypeptide from a recombinant expression vector comprising a nucleic acid encoding the polypeptide, wherein the amino acid sequence of the polypeptide comprises greater than about 70% amino acid identity to a polypeptide having an amino acid sequence of SEQ ID NO:2, SEQ ID NO:4, SEQ ID NO:6 or SEQ ID NO:8.

In another aspect, the present invention provides a method of making a recombinant cell comprising a G-protein coupled receptor polypeptide, the method comprising the step of transducing the cell with an expression vector comprising a nucleic acid encoding the polypeptide, wherein the amino acid sequence of the polypeptide comprises greater than about 70% amino acid identity to a polypeptide having an amino acid sequence of SEQ ID NO:2, SEQ ID NO:4, SEQ ID NO:6, or SEQ ID NO:8.

BRIEF DESCRIPTION OF THE DRAWINGS

FIG. 1: Breast cancer tumors and cell lines with amplified copies of the BCA-GPCR-3 gene.

FIG. 3: Quantitative data of BCA-GPCR-3 mRNA overexpression in breast cancer tissue and breast cancer cell lines. The designation 'Me' refers to normal mammary epithelial cells. 'MG' refers to normal mammary gland tissue.

DETAILED DESCRIPTION OF THE INVENTION

Introduction

Figure 2:
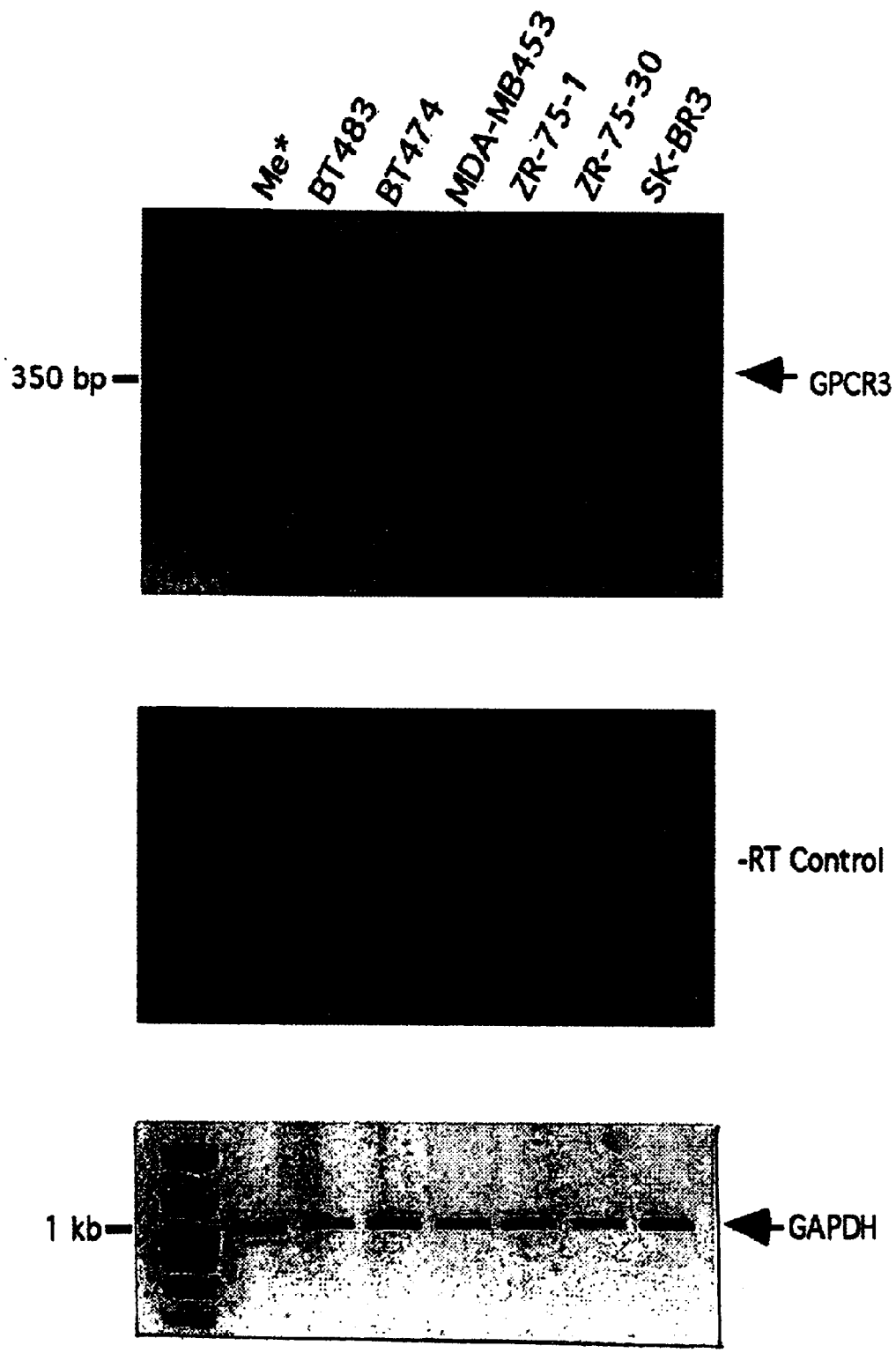
FIG. 2: BCA-GPCR-3 mRNA overexpression in breast cancer cell lines. The designation 'Me' refers to normal mammary epithelial cells.

The present invention provides for the first time nucleic acids encoding four novel G protein coupled receptors. These nucleic acids and the receptors that they encode are referred individually designated as BCA-GPCR-1, 2, 3, and 4. These BCA-GPCRs are components of signal transduction pathways and are associated with a genomic region amplified in breast cancer cells. These nucleic acids provide valuable probes for the identification of breast cancer cells, as the nucleic acids are specifically amplified in certain breast cancer cells or are very close (within 100 kb) or regions that are specifically amplified and/or overexpressed in breast cancer cells. Nucleic acids encoding the BCA-GPCRs of the invention can be identified using techniques such as reverse transcription and amplification of mRNA, isolation of total RNA or poly $A^+$ RNA, northern blotting, dot blotting, in situ hybridization, RNase protection, S1 digestion, probing DNA microchip arrays, and the like.

Chromosome localization of the genes has been determined, and all four of the genes are located at chromosome 1q44 in the following orientation, starting from the centromere end, 5' to 3' strand: BCA-GPCR-1 (3'–5' orientation); approx. 40 kb; BCA-GPCR-2 (5' to 3' orientation); approx. 40 kb; BCA-GPCR-3, (3'–5' orientation); approx. 60 kb; BCA-GPCR-4 (5' to 3' orientation), ending with the telomere end. These genes encoding human BCA-GPCRs can be used to identify diseases, mutations, and traits caused by and associated with BCA-GPCRs, such as cancer, e.g., breast cancer. The BCA-GPCRs of the invention are also useful for cancer diagnostics, in particular breast cancer.

The isolation of novel BCA-GPCRs provides a means for assaying for and identifying modulators of G-protein coupled receptor signal transduction, e.g., activators, inhibitors, stimulators, enhancers, agonists, and antagonists. Such modulators of signal transduction are useful for pharmacological modulation of signaling pathways, e.g., in cancer cells such as breast cancer. Such activators and inhibitors identified using BCA-GPCRs can also be used to further study signal transduction. Thus, the invention provides assays for signal transduction modulation, where the BCA-GPCRs act as direct or indirect reporter molecules for the effect of modulators on signal transduction. BCA-GPCRs can be used in assays in vitro, ex vivo, and in vivo, e.g., to measure changes in transcriptional activation of GPCRs; ligand binding; phosphorylation and dephosphorylation; GPCR binding to G-proteins; G-protein activation; regulatory molecule binding; voltage, membrane potential, and conductance changes; ion flux; changes in intracellular second messengers such as cAMP and inositol triphosphate; changes in intracellular calcium levels; and neurotransmitter release.

Methods of assaying for modulators of signal transduction include in vitro ligand binding assays using the BCA- GPCRs, portions thereof such as the extracellular domain, or chimeric proteins comprising one or more domains of a GPCR, oocyte GPCR expression or tissue culture cell GPCR expression, either naturally occurring or recombinant; membrane expression of a GPCR, either naturally occurring or recombinant; tissue expression of a GPCR; expression of a GPCR in a transgenic animal, etc.

Functionally, the BCA-GPCRs represent a seven transmembrane G-protein coupled receptor of the G-protein coupled receptor family, which interact with a G protein to mediate signal transduction (see, e.g., Fong, *Cell Signal* 8:217 (1996); Baldwin, *Curr. Opin. Cell Biol.* 6:180 (1994)). The genes encoding the BCA-GPCRs are on chromosome 1q44 and are associated with a region that is amplified in breast cancer cells.

Structurally, the nucleotide sequence of human BCA-GPCR-1 (see, e.g., SEQ ID NO:1, encodes a polypeptide with a predicted molecular weight of approximately 31 kDa and a predicted range of 26–36 kDa (see, e.g., SEQ ID NO:2). Related BCA-GPCR-1 genes from other species should share at least about 70% amino acid identity over a amino acid region at least about 25 amino acids in length, optionally 50 to 100 amino acids in length.

The present invention also provides polymorphic variants of the BCA-GPCR-1 depicted in SEQ ID NO:1: variant #1, in which an leucine residue is substituted for a isoleucine acid residue at amino acid position 7 from the methionine; variant #2, in which an aspartic acid residue is substituted for a glutamic acid residue at amino acid position 142 from the methionine; and variant #3, in which a glycine residue is substituted for an alanine acid residue at amino acid position 6 from the methionine.

Structurally, the nucleotide sequence of human BCA-GPCR-2 (see, e.g., SEQ ID NO:3 encodes a polypeptide with a predicted molecular weight of approximately 37 kDa and a predicted range of 32–42 kDa (see, e.g., SEQ ID NO:4). Related BCA-GPCR-2 genes from other species should share at least about 70% amino acid identity over a amino acid region at least about 25 amino acids in length, optionally 50 to 100 amino acids in length. BCA-GPCR-2 is amplified at least about 2–3 fold in 15% of primary breast tumors and tumor cell lines.

The present invention also provides polymorphic variants of the BCA-GPCR-2 depicted in SEQ ID NO:4: variant #1, in which an isoleucine residue is substituted for a leucine acid residue at amino acid position 9; variant #2, in which an glutamic acid residue is substituted for a aspartic acid residue at amino acid position 19; and variant #3, in which a glycine residue is substituted for an alanine residue at amino acid position 6.

Structurally, the nucleotide sequence of human BCA-GPCR-3 (see, e.g., SEQ ID NO:5, expressed in placenta and testis) encodes a polypeptide with a predicted molecular weight of approximately 37 kDa and a predicted range of 32–42 kDa (see, e.g., SEQ ID NO:6). Related BCA-GPCR-3 genes from other species should share at least about 70% amino acid identity over a amino acid region at least about 25 amino acids in length, optionally 50 to 100 amino acids in length. BCA-GPCR-3 is amplified at least about 3–7 fold in about 15% of primary breast tumors and tumor cell lines (see FIG. 1). In addition, BCA-GPCR-3 mRNA levels are elevated in breast cancer cell lines from both amplified and non-amplified tumors (see FIGS. 2–3).

The present invention also provides polymorphic variants of the BCA-GPCR-3 depicted in SEQ ID NO:6: variant #1, in which an isoleucine residue is substituted for a leucine acid residue at amino acid position 8; variant #2, in which an glutamic acid residue is substituted for a aspartic acid residue at amino acid position 73; and variant #3, in which a glycine residue is substituted for an alanine residue at amino acid position 7.

Structurally, the nucleotide sequence of human BCA-GPCR-4 (see, e.g., SEQ ID NO:7 encodes a polypeptide with a predicted molecular weight of approximately 37 kDa and a predicted range of 32–42 kDa (see, e.g., SEQ ID NO:8). Related BCA-GPCR-4 genes from other species should share at least about 70% amino acid identity over a amino acid region at least about 25 amino acids in length, optionally 50 to 100 amino acids in length. BCA-GPCR-4 is amplified at least about 2–3 fold in 15% of primary breast tumors and tumor cell lines.

The present invention also provides polymorphic variants of the BCA-GPCR-4 depicted in SEQ ID NO:8: variant #1, in which an isoleucine residue is substituted for a leucine acid residue at amino acid position 7; variant #2, in which an aspartic acid residue is substituted for a glutamic acid residue at amino acid position 13; and variant #3, in which a glycine residue is substituted for an serine residue at amino acid position 10.

Specific regions of the BCA-GPCR nucleotide and amino acid sequences may be used to identify polymorphic variants, interspecies homologs, and alleles of BCA-GPCRs. This identification can be made in vitro, e.g., under stringent hybridization conditions or PCR (using primers that hybridize to SEQ ID NOS:1, 3, 5, and 7, e.g., SEQ ID NOS:9–16) and sequencing, or by using the sequence information in a computer system for comparison with other nucleotide sequences. Typically, identification of polymorphic variants and alleles of an BCA-GPCR is made by comparing an amino acid sequence of about 25 amino acids or more, e.g., 50–100 amino acids. Amino acid identity of approximately at least 70% or above, optionally 75%, 80%, 85% or 90–95% or above typically demonstrates that a protein is a polymorphic variant, interspecies homolog, or allele of an BCA-GPCR. Sequence comparison is performed using the BLAST and BLAST 2.0 sequence comparison algorithms with default parameters, discussed below. Antibodies that bind specifically to an BCA-GPCR or a conserved region thereof can also be used to identify alleles, interspecies homologs, and polymorphic variants. The polymorphic variants, alleles and interspecies homologs are expected to retain the seven transmembrane structure of a G-protein coupled receptor.

BCA-GPCR nucleotide and amino acid sequence information may also be used to construct models of BCA-GPCRs in a computer system. These models are subsequently used to identify compounds that can activate or inhibit BCA-GPCRs. Such compounds that modulate the activity of an BCA-GPCR can be used to investigate the role of BCA-GPCRs in signal transduction.

Definitions

"BCA-GPCR" and "BCA-GPCR-1, 2, 3, or 4" refer to novel G-protein coupled receptors, the genes for which are located on chromosome 1q44 and are associated with a region of the chromosome that is amplified in breast cancer cells. The BCA-GPCRs of the invention have seven transmembrane regions and have "G-protein coupled receptor activity," e.g., they bind to G-proteins in response to extracellular stimuli and promote production of second messengers such as IP3, cAMP, and $Ca^{2+}$ via stimulation of downstream effectors such as phospholipase C and adenylate cyclase (for a description of the structure and function of GPCRs, see, e.g., Fong, supra, and Baldwin, supra).

Topologically, BCA-GPCRs have an N-terminal "extracellular domain," a "transmembrane domain" comprising seven transmembrane regions and corresponding cytoplasmic and extracellular loops, and a C-terminal "cytoplasmic domain" (see, e.g., Buck & Axel, *Cell* 65:175–187 (1991)). These domains can be structurally identified using methods known to those of skill in the art, such as sequence analysis programs that identify hydrophobic and hydrophilic domains (see, e.g., Kyte & Doolittle, *J. Mol. Biol.* 157:105–132 (1982)). Such domains are useful for making chimeric proteins and for in vitro assays of the invention.

"Extracellular domain" therefore refers to the domain of an BCA-GPCR that protrudes from the cellular membrane and often binds to an extracellular ligand. This domain is often useful for in vitro ligand binding assays, both soluble and solid phase.

"Transmembrane domain," comprises seven transmembrane regions plus the corresponding cytoplasmic and extracellular loops. Certain regions of the transmembrane domain can also be involved in ligand binding.

"Cytoplasmic domain" refers to the domain of an BCA-GPCR that protrudes into the cytoplasm after the seventh transmembrane region and continues to the C-terminus of the polypeptide.

"GPCR activity" refers to the ability of a GPCR to transduce a signal. Such activity can be measured, e.g., in a heterologous cell, by coupling a GPCR (or a chimeric GPCR) to a G-protein and a downstream effector such as PLC, and measuring increases in intracellular calcium (see, e.g., Offermans & Simon, *J. Biol. Chem.* 270:15175–15180 (1995)). Receptor activity can be effectively measured by recording ligand-induced changes in $[Ca^{2+}]_i$ using fluorescent $Ca^{2+}$-indicator dyes and fluorometric imaging.

The terms "BCA-GPCR" and "BCA-GPCR-1, 2, 3, or 4" therefore refer to polymorphic variants, alleles, mutants, and interspecies homologs and BCA-GPCR domains thereof that: (1) have about 70% amino acid sequence identity, preferably about 75, 80, 85, 90 or 95% or higher amino acid sequence identity, to SEQ ID NO:2, 4, 6, or 8 over a window of about 25 amino acids, preferably 50–100 amino acids; (2) bind to antibodies raised against an immunogen comprising an amino acid sequence of SEQ ID NO:2, 4, 6, or 8 and conservatively modified variants thereof; or (3) specifically hybridize (with a size of at least about 100, preferably at least about 500 or 1000 nucleotides) under stringent hybridization conditions to a sequence SEQ ID NO:1, 3, 5, or 7, and conservatively modified variants thereof. This term also refers to a domain of an BCA-GPCR, as described above., or a fusion protein comprising a domain of an BCA-GPCR linked to a heterologous protein A "host cell" is a naturally occurring cell or a transformed cell that contains an expression vector and supports the replication or expression of the expression vector. Host cells may be cultured cells, explants, cells in vivo, and the like. Host cells may be prokaryotic cells such as *E. coli*, or eukaryotic cells such as yeast, insect, amphibian, or mammalian cells such as CHO, HeLa, and the like.

"Biological sample" as used herein is a sample of biological tissue or fluid that contains nucleic acids or polypeptides of novel BCA-GPCRs. Such samples include, but are not limited to, tissue isolated from humans, mice, and rats,. Biological samples may also include sections of tissues such as frozen sections taken for histologic purposes. A biological sample is typically obtained from a eukaryotic organism, such as insects, rotozoa, birds, fish, reptiles, and preferably a mammal such as rat, mouse, cow, dog, guinea pig, or rabbit, and most preferably a primate such as chimpanzees or humans. referred tissues include e.g., normal prostate epithelial tissue, placenta, and testis tissue.

The phrase "functional effects" in the context of assays for testing compounds that modulate BCA-GPCR-mediated signal transduction includes the determination of any parameter that is indirectly or directly under the influence of an BCA-GPCR, e.g., a functional, physical, or chemical effect. It includes ligand binding, changes in ion flux, membrane potential, current flow, transcription, G-protein binding, gene amplification, expression in cancer cells, GPCR phosphorylation or dephosphorylation, signal transduction, receptor-ligand interactions, second messenger concentrations (e.g., cAMP, cGMP, $IP_3$, or intracellular $Ca^{2+}$), in vitro, in vivo, and ex vivo and also includes other physiologic effects such increases or decreases of neurotransmitter or hormone release.

By "determining the functional effect" is meant assays for a compound that increases or decreases a parameter that is indirectly or directly under the influence of an BCA-GPCR, e.g., functional, physical and chemical effects. Such functional effects can be measured by any means known to those skilled in the art, e.g., changes in spectroscopic characteristics (e.g., fluorescence, absorbance, refractive index), hydrodynamic (e.g., shape), chromatographic, or solubility properties, patch clamping, voltage-sensitive dyes, whole cell currents, radioisotope efflux, inducible markers, transcriptional activation of BCA-GPCRs; ligand binding assays; voltage, membrane potential and conductance changes; ion flux assays; changes in intracellular second messengers such as cAMP and inositol triphosphate (IP3); changes in intracellular calcium levels; neurotransmitter release, and the like.

"Inhibitors," "activators," and "modulators" of BCA-GPCRs are used interchangeably to refer to inhibitory, activating, or modulating molecules identified using in vitro and in vivo assays for signal transduction, e.g., ligands, agonists, antagonists, and their homologs and mimetics. Inhibitors are compounds that, e.g., bind to, partially or totally block stimulation, decrease, prevent, delay activation, inactivate, desensitize, or down regulate signal transduction, e.g., antagonists. Activators are compounds that, e.g., bind to, stimulate, increase, open, activate, facilitate, enhance activation, sensitize or up regulate signal transduction, e.g., agonists. Modulators include compounds that, e.g., alter the interaction of a polypeptide with: extracellular proteins that bind activators or inhibitor; G-proteins; G protein alpha, beta, and gamma subunits; and kinases. Modulators also include genetically modified versions of BCA-GPCRs, e.g., with altered activity, as well as naturally occurring and synthetic ligands, antagonists, agonists, antibodies, small chemical molecules and the like. Such assays for inhibitors and activators include, e.g., expressing BCA-GPCRs in vitro, in cells, or cell membranes, applying putative modulator compounds, and then determining the functional effects on signal transduction, as described above.

Samples or assays comprising BCA-GPCRs that are treated with a potential activator, inhibitor, or modulator are compared to control samples without the inhibitor, activator, or modulator to examine the extent of inhibition. Control samples (untreated with inhibitors) are assigned a relative BCA-GPCR activity value of 100%. Inhibition of an BCA-GPCR is achieved when the BCA-GPCR activity value relative to the control is about 80%, preferably 50%, more preferably 25–0%. Activation of an BCA-GPCR is achieved when the BCA-GPCR activity value relative to the control (untreated with activators) is 110%, more preferably 150%, more preferably 200–500% (i.e., two to five fold higher relative to the control), more preferably 1000–3000% higher.

The terms "isolated" "purified" or "biologically pure" refer to material that is substantially or essentially free from components which normally accompany it as found in its native state. Purity and homogeneity are typically determined using analytical chemistry techniques such as polyacrylamide gel electrophoresis or high performance liquid chromatography. A protein that is the predominant species present in a preparation is substantially purified. In particular, an isolated BCA-GPCR nucleic acid is separated from open reading frames that flank the BCA-GPCR gene and encode proteins other than the BCA-GPCR. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure.

"Biologically active" BCA-GPCR refers to an BCA-GPCR having signal transduction activity and G protein coupled receptor activity, as described above.

"Nucleic acid" refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixedase and/or deoxyinosine residues (Batzer et al., *Nucleic Acid Res.* 19:5081 (1991); Ohtsuka et al., *J. Biol. Chem.* 260:2605–2608 (1985); Rossolini et al., *Mol. Cell. Probes* 8:91–98 (1994)). The term nucleic acid is used interchangeably with gene, cDNA, mRNA, oligonucleotide, and polynucleotide.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, *Proteins* (1984)).

Macromolecular structures such as polypeptide structures can be described in terms of various levels of organization. For a general discussion of this organization, see, e.g., Alberts et al., *Molecular Biology of the Cell* ($3^{rd}$ ed., 1994) and Cantor and Schimmel, *Biophysical Chemistry Part I. The Conformation of Biological Macromolecules* (1980).

"Primary structure" refers to the amino acid sequence of a particular peptide. "Secondary structure" refers to locally ordered, three dimensional structures within a polypeptide. These structures are commonly known as domains. Domains are portions of a polypeptide that form a compact unit of the polypeptide and are typically 25 to approximately 500 amino acids long. Typical domains are made up of sections of lesser organization such as stretches of β-sheet and α-helices. "Tertiary structure" refers to the complete three dimensional structure of a polypeptide monomer. "Quaternary structure" refers to the three dimensional structure formed by the noncovalent association of independent tertiary units. Anisotropic terms are also known as energy terms.

A "label" or a "detectable moiety" is a composition detectable by spectroscopic, photochemical, biochemical, immunochemical, or chemical means. For example, useful labels include $^{32}P$, fluorescent dyes, electron-dense reagents, enzymes (e.g., as commonly used in an ELISA), biotin, digoxigenin, or haptens and proteins for which ant or 7 can be made detectable, e.g., by incorporating a radiolabel into the peptide, and used to detect antibodies specifically reactive with the peptide).

A "labeled nucleic acid probe or oligonucleotide" is one that is bound, either covalently, through a linker or a chemical bond, or noncovalently, through ionic, van der Waals, electrostatic, or hydrogen bonds to a label such that the presence of the probe may be detected by detecting the presence of the label bound to the probe.

As used herein a "nucleic acid probe or oligonucleotide" is defined as a nucleic acid capable of binding to a target nucleic acid of complementary sequence through one or more types of chemical bonds, usually through complementary base pairing, usually through hydrogen bond formation. As used herein, a probe may include natural (i.e., A, G, C, or T) or modified bases (7-deazaguanosine, inosine, etc.). In addition, the bases in a probe may be joined by a linkage other than a phosphodiester bond, so long as it does not interfere with hybridization. Thus, for example, probes may be peptide nucleic acids in which the constituent bases are joined by peptide bonds rather than phosphodiester linkages. It will be understood by one of skill in the art that probes may bind target sequences lacking complete complementarity with the probe sequence depending upon the stringency of the hybridization conditions. The probes are preferably directly labeled as with isotopes, chromophores, lumiphores, chromogens, or indirectly labeled such as with biotin to which a streptavidin complex may later bind. By assaying for the presence or absence of the probe, one can detect the presence or absence of the select sequence or subsequence.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

A "promoter" is defined as an array of nucleic acid control sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. A "constitutive" promoter is a promoter that is active under most environmental and developmental conditions. An "inducible" promoter is a promoter that is active under environmental or developmental regulation. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

An "expression vector" is a nucleic acid construct, generated recombinantly or synthetically, with a series of specified nucleic acid elements that permit transcription of a particular nucleic acid in a host cell. The expression vector can be part of a plasmid, virus, or nucleic acid fragment. Typically, the expression vector includes a nucleic acid to be transcribed operably linked to a promoter.

The terms "identical" or percent "identity," in the context of two or more nucleic acids or polypeptide sequences, refer to two or more sequences or subsequences that are the same or have a specified percentage of amino acid residues or nucleotides that are the same (i.e., about 70% identity, preferably 75%, 80%, 85%, 90%, or 95% identity over a specified region, when compared and aligned for maximum correspondence over a comparison window, or designated region as measured using a BLAST or BLAST 2.0 sequence comparison algorithms with default parameters described below, or by manual alignment and visual inspection. Such sequences are then said to be "substantially identical." This definition also refers to the compliment of a test sequence. Preferably, the identity exists over a region that is at least about 25 amino acids or nucleotides in length, or more preferably over a region that is 50–100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

A preferred example of algorithm that is suitable for determining percent sequence identity and sequence similarity are the BLAST and BLAST 2.0 algorithms, which are described in Altschul et al., *Nuc. Acids Res.* 25:3389–3402 (1977) and Altschul et al., *J. Mol. Biol.* 215:403–410 (1990), respectively. BLAST and BLAST 2.0 are used, with the parameters described herein, to determine percent sequence identity for the nucleic acids and proteins of the invention. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, *Proc. Nat'l. Acad. Sci. USA* 90:5873–5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

Another example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle, *J. Mol. Evol.* 35:351–360 (1987). The method used is similar to the method described by Higgins & Sharp, *CABIOS* 5:151–153 (1989). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, e.g., version 7.0 (Devereaux et al., *Nuc. Acids Res.* 12:387–395 (1984).

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5–10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency.

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kDa) and one "heavy" chain (about 50–70 kDa). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce F(ab)'$_2$, a dimer of Fab which itself is a light chain joined to $V_H$-$C_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region (see *Fundamental Immunology* (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552–554 (1990)).

For preparation of monoclonal or polyclonal antibodies, any technique known in the art can be used (see, e.g., Kohler & Milstein, *Nature* 256:495–497 (1975); Kozbor et al., *Immunology Today* 4: 72 (1983); Cole et al., pp. 77–96 in *Monoclonal Antibodies and Cancer Therapy* (1985)). Techniques for the production of single chain antibodies (U.S. Pat. No. 4,946,778) can be adapted to produce antibodies to polypeptides of this invention. Also, transgenic mice, or other organisms such as other mammals, may be used to express humanized antibodies. Alternatively, phage display technology can be used to identify antibodies and heteromeric Fab fragments that specifically bind to selected antigens (see, e.g., McCafferty et al., *Nature* 348:552–554 (1990); Marks et al., *Biotechnology* 10:779–783 (1992)).

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

An "anti-BCA-GPCR" antibody is an antibody or antibody fragment that specifically binds a polypeptide encoded by an BCA-GPCR gene, cDNA, or a subsequence thereof The term "immunoassay" is an assay that uses an antibody to specifically bind an antigen. The immunoassay is characterized by the use of specific binding properties of a particular antibody to isolate, target, and/or quantify the antigen.

The phrase "specifically (or selectively) binds" to an antibody or "specifically (or selectively) immunoreactive with," when referring to a protein or peptide, refers to a binding reaction that is determinative of the presence of the protein in a heterogeneous population of proteins and other biologics. Thus, under designated immunoassay conditions, the specified antibodies bind to a particular protein at least two times the background and do not substantially bind in a significant amount to other proteins present in the sample. Specific binding to an antibody under such conditions may require an antibody that is selected for its specificity for a particular protein. For example, polyclonal antibodies raised to a particular BCA-GPCR can be selected to obtain only those polyclonal antibodies that are specifically immunoreactive with the BCA-GPCR, and not with other proteins, except for polymorphic variants, orthologs, and alleles of the BCA-GPCR. This selection may be achieved by subtracting out antibodies that cross-react with BCA-GPCR molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, *Antibodies, A Laboratory Manual* (1988), for a description of immunoassay formats and conditions that can be used to determine specific immunoreactivity). Typically a specific or selective reaction will be at least twice background signal or noise and more typically more than 10 to 100 times background. Antibodies that react only with a particular BCA-GPCR ortholog, e.g., from specific species such as rat, mouse, or human, can also be made as described above, by subtracting out antibodies that bind to the same BCA-GPCR from another species.

The phrase "selectively associates with" refers to the ability of a nucleic acid to "selectively hybridize" with another as defined above, or the ability of an antibody to "selectively (or specifically) bind to a protein, as defined above.

Isolation of Nucleic Acids Encoding BCA-GPCRs
A. General Recombinant DNA Methods This invention relies on routine techniques in the field of recombinant genetics. Basic texts disclosing the general methods of use in this invention include Sambrook et al., *Molecular Cloning, A Laboratory Manual* (2nd ed. 1989); Kriegler, *Gene Transfer and Expression: A Laboratory Manual* (1990); and *Current Protocols in Molecular Biology* (Ausubel et al., eds., 1994)).

For nucleic acids, sizes are given in either kilobases (kb) or base pairs (bp). These are estimates derived from agarose or acrylamide gel electrophoresis, from sequenced nucleic acids, or from published DNA sequences. For proteins, sizes are given in kilodaltons (kDa) or amino acid residue numbers. Proteins sizes are estimated from gel electrophoresis, from sequenced proteins, from derived amino acid sequences, or from published protein sequences.

Oligonucleotides that are not commercially available can be chemically synthesized according to the solid phase phosphoramidite triester method first described by Beaucage & Caruthers, *Tetrahedron Letts.* 22:1859–1862 (1981), using an automated synthesizer, as described in Van Devanter et. al., *Nucleic Acids Res.* 12:6159–6168 (1984). Purification of oligonucleotides is by either native acrylamide gel electrophoresis or by anion-exchange HPLC as described in Pearson & Reanier, *J. Chrom.* 255:137–149 (1983).

The sequence of the cloned genes and synthetic oligonucleotides can be verified after cloning using, e.g., the chain termination method for sequencing double-stranded templates of Wallace et al., *Gene* 16:21–26 (1981).

B. Cloning Methods for the Isolation of Nucleotide Sequences Encoding BCA-GPCRs

In general, the nucleic acid sequences encoding BCA-GPCRs and related nucleic acid sequence homologs are cloned from cDNA and genomic DNA libraries by hybridization with a probe, or isolated using amplification techniques with oligonucleotide primers. For example, BCA-GPCR sequences are typically isolated from mammalian nucleic acid (genomic or cDNA) libraries by hybridizing with a nucleic acid probe, the sequence of which can be derived from SEQ ID NOS:1, 3, 5, or 7. Suitable tissues from which BCA-GPCR RNA and cDNA can be isolated include, e.g., breast cancer cells, normal prostate epithelial cells, placenta, or testis.

Amplification techniques using primers can also be used to amplify and isolate BCA-GPCR nucleic acids from DNA or RNA. The degenerate primers encoding the following amino acid sequences can also be used to amplify a sequence of a BCA-GPCR: SEQ ID NOS:9–16 (see, e.g., Dieffenfach & Dveksler, *PCR Primer: A Laboratory Manual* (1995)). These primers can be used, e.g., to amplify either the full length sequence or a probe of one to several hundred nucleotides, which is then used to screen a mammalian library for full-length BCA-GPCRs.

Nucleic acids encoding BCA-GPCRs can also be isolated from expression libraries using antibodies as probes. Such polyclonal or monoclonal antibodies can be raised using the sequence of SEQ ID NOS:2, 4, 6, or 8.

BCA-GPCR polymorphic variants, alleles, and interspecies homologs that are substantially identical to an BCA-GPCR can be isolated using BCA-GPCR nucleic acid probes, and oligonucleotides under stringent hybridization conditions, by screening libraries. Alternatively, expression libraries can be used to clone BCA-GPCRs and BCA-GPCR polymorphic variants, alleles, and interspecies homologs, by detecting expressed homologs immunologically with antisera or purified antibodies made against BCA-GPCRs, which also recognize and selectively bind to the BCA-GPCR homolog.

To make a cDNA library, one should choose a source that is rich in BCA-GPCR mRNA. The mRNA is then made into cDNA using reverse transcriptase, ligated into a recombinant vector, and transfected into a recombinant host for propagation, screening and cloning. Methods for making and screening cDNA libraries are well known (see, e.g., Gubler & Hoffman, *Gene* 25:263–269 (1983); Sambrook et al., supra; Ausubel et al., supra).

For a genomic library, the DNA is extracted from the tissue and either mechanically sheared or enzymatically digested to yield fragments of about 12–20 kb. The fragments are then separated by gradient centrifugation from undesired sizes and are constructed in bacteriophage lambda vectors. These vectors and phage are packaged in vitro. Recombinant phage are analyzed by plaque hybridization as described in Benton & Davis, *Science* 196:180–182 (1977). Colony hybridization is carried out as generally described in Grunstein et al., *Proc. Natl. Acad. Sci. USA.*, 72:3961–3965 (1975).

An alternative method of isolating BCA-GPCR nucleic acids and their homologs combines the use of synthetic oligonucleotide primers and amplification of an RNA or DNA template (see U.S. Pat. Nos. 4,683,195 and 4,683,202; *PCR Protocols: A Guide to Methods and Applications* (Innis et al., eds, 1990)). Methods such as polymerase chain reaction (PCR) and ligase chain reaction (LCR) can be used to amplify nucleic acid sequences of BCA-GPCRs directly from mRNA, from cDNA, from genomic libraries or cDNA libraries. Degenerate oligonucleotides can be designed to amplify BCA-GPCR homologs using the sequences provided herein. Restriction endonuclease sites can be incorporated into the primers. Polymerase chain reaction or other in vitro amplification methods may also be useful, for example, to clone nucleic acid sequences that code for proteins to be expressed, to make nucleic acids to use as probes for detecting the presence of BCA-GPCR-encoding mRNA in physiological samples, for nucleic acid sequencing, or for other purposes. Genes amplified by the PCR reaction can be purified from agarose gels and cloned into an appropriate vector.

Gene expression of BCA-GPCRs can also be analyzed by techniques known in the art, e.g., reverse transcription and amplification of mRNA, isolation of total RNA or poly $A^+$ RNA, northern blotting, dot blotting, in situ hybridization, RNase protection, probing DNA microchip arrays, and the like. In one embodiment, high density oligonucleotide analysis technology (e.g., GeneChip™) is used to identify homologs and polymorphic variants of the GPCRs of the invention. In the case where the homologs being identified are linked to a known disease, they can be used with GeneChip™ as a diagnostic tool in detecting the disease in a biological sample, see, e.g., Gunthand et al., *AIDS Res. Hum. Retroviruses* 14: 869–876 (1998); Kozal et al., *Nat. Med.* 2:753–759 (1996); Matson et al., *Anal. Biochem.* 224:110–106 (1995); Lockhart et al., *Nat. Biotechnol.* 14:1675–1680 (1996); Gingeras et al., *Genome Res.* 8:435–448 (1998); Hacia et al., *Nucleic Acids Res.* 26:3865–3866 (1998).

Synthetic oligonucleotides can be used to construct recombinant BCA-GPCR genes for use as probes or for expression of protein. This method is performed using a series of overlapping oligonucleotides usually 40–120 bp in length, representing both the sense and nonsense strands of the gene. These DNA fragments are then annealed, ligated and cloned. Alternatively, amplification techniques can be used with precise primers to amplify a specific subsequence of the BCA-GPCR nucleic acid. The specific subsequence is then ligated into an expression vector.

The nucleic acid encoding an BCA-GPCR is typically cloned into intermediate vectors before transformation into prokaryotic or eukaryotic cells for replication and/or expression. These intermediate vectors are typically prokaryote vectors, e.g., plasmids, or shuttle vectors.

Optionally, nucleic acids encoding chimeric proteins comprising BCA-GPCRs or domains thereof can be made according to standard techniques. For example, a domain such as ligand binding domain, an extracellular domain, a transmembrane domain (e.g., one comprising seven transmembrane regions and corresponding extracellular and cytosolic loops), the transmembrane domain and a cytoplasmic domain, an active site, a subunit association region, etc., can be covalently linked to a heterologous protein. For example, an extracellular domain can be linked to a heterologous GPCR transmembrane domain, or a heterologous GPCR extracellular domain can be linked to a transmembrane domain. Other heterologous proteins of choice include, e.g., green fluorescent protein, luciferase, or β-gal.

C. Expression in Prokaryotes and Eukaryotes

To obtain high level expression of a cloned gene or nucleic acid, such as those cDNAs encoding BCA-GPCRs, one typically subclones an BCA-GPCR into an expression vector that contains a strong promoter to direct transcription, a transcription/translation terminator, and if for a nucleic acid encoding a protein, a ribosome binding site for translational initiation. Suitable bacterial promoters are well known in the art and described, e.g., in Sambrook et al. and Ausubel et al. Bacterial expression systems for expressing the BCA-GPCR protein are available in, e.g., *E. coli*, *Bacillus sp.*, and *Salmonella* (Palva et al., *Gene* 22:229–235 (1983); Mosbach et al., *Nature* 302:543–545 (1983). Kits for such expression systems are commercially available. Eukaryotic expression systems for mammalian cells, yeast, and insect cells are well known in the art and are also commercially available. In one embodiment, the eukaryotic expression vector is an adenoviral vector, an adeno-associated vector, or a retroviral vector.

The promoter used to direct expression of a heterologous nucleic acid depends on the particular application. The promoter is optionally positioned about the same distance from the heterologous transcription start site as it is from the transcription start site in its natural setting. As is known in the art, however, some variation in this distance can be accommodated without loss of promoter function.

In addition to the promoter, the expression vector typically contains a transcription unit or expression cassette that contains all the additional elements required for the expression of the BCA-GPCR encoding nucleic acid in host cells. A typical expression cassette thus contains a promoter operably linked to the nucleic acid sequence encoding an BCA-GPCR and signals required for efficient polyadenylation of the transcript, ribosome binding sites, and translation termination. The nucleic acid sequence encoding an BCA-GPCR may typically be linked to a cleavable signal peptide sequence to promote secretion of the encoded protein by the transformed cell. Such signal peptides would include, among others, the signal peptides from tissue plasminogen activator, insulin, and neuron growth factor, and juvenile hormone esterase of *Heliothis virescens*. Additional elements of the cassette may include enhancers and, if genomic DNA is used as the structural gene, introns with functional splice donor and acceptor sites.

In addition to a promoter sequence, the expression cassette should also contain a transcription termination region downstream of the structural gene to provide for efficient termination. The termination region may be obtained from the same gene as the promoter sequence or may be obtained from different genes.

The particular expression vector used to transport the genetic information into the cell is not particularly critical. Any of the conventional vectors used for expression in eukaryotic or prokaryotic cells may be used. Standard bacterial expression vectors include plasmids such as pBR322 based plasmids, pSKF, pET23D, and fusion expression systems such as GST and LacZ. Epitope tags can also be added to recombinant proteins to provide convenient methods of isolation, e.g., c-myc.

Expression vectors containing regulatory elements from eukaryotic viruses are typically used in eukaryotic expression vectors, e.g., SV40 vectors, papilloma virus vectors, and vectors derived from Epstein-Barr virus. Other exemplary eukaryotic vectors include pMSG, pAV009/A$^+$, pMTO10/A$^+$, pMAMneo-5, baculovirus pDSVE, and any other vector allowing expression of proteins under the direction of the SV40 early promoter, SV40 later promoter, metallothionein promoter, murine mammary tumor virus promoter, Rous sarcoma virus promoter, polyhedrin promoter, or other promoters shown effective for expression in eukaryotic cells.

Some expression systems have markers that provide gene amplification such as thymidine kinase, hygromycin B phosphotransferase, and dihydrofolate reductase. Alternatively, high yield expression systems not involving gene amplification are also suitable, such as using a baculovirus vector in insect cells, with an BCA-GPCR-encoding sequence under the direction of the polyhedrin promoter or other strong baculovirus promoters.

The elements that are typically included in expression vectors also include a replicon that functions in *E. coli*, a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical, any of the many resistance genes known in the art are suitable. The prokaryotic sequences are optionally chosen such that they do not interfere with the replication of the DNA in eukaryotic cells, if necessary.

Standard transfection methods are used to produce bacterial, mammalian, yeast or insect cell lines that express large quantities of BCA-GPCR protein, which are then purified using standard techniques (see, e.g., Colley et al., *J. Biol. Chem.* 264:17619–17622 (1989); *Guide to Protein Purification*, in *Methods in Enzymology*, vol. 182 (Deutscher, ed., 1990)). Transformation of eukaryotic and prokaryotic cells are performed according to standard techniques (see, e.g., Morrison, *J. Bact.* 132:349–351 (1977); Clark-Curtiss & Curtiss, *Methods in Enzymology* 101:347–362 (Wu et al., eds, 1983).

Any of the well known procedures for introducing foreign nucleotide sequences into host cells may be used. These include the use of calcium phosphate transfection, polybrene, protoplast fusion, electroporation, liposomes, microinjection, plasma vectors, viral vectors and any of the other well known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing an BCA-GPCR.

After the expression vector is introduced into the cells, the transfected cells are cultured under conditions favoring expression of an BCA-GPCR, which is recovered from the culture using standard techniques identified below.

Purification of BCA-GPCRs

Either naturally occurring or recombinant BCA-GPCRs can be purified for use in functional assays. Optionally, recombinant BCA-GPCRs are purified. Naturally occurring BCA-GPCRs are purified, e.g., from any suitable tissue or cell expressing naturally occurring BCA-GPCRs. Recombinant BCA-GPCRs are purified from any suitable bacterial or eukaryotic expression system, e.g., CHO cells or insect cells.

An BCA-GPCR may be purified to substantial purity by standard techniques, including selective precipitation with such substances as ammonium sulfate; column chromatography, immunopurification methods, and others (see, e.g., Scopes, *Protein Purification: Principles and Practice* (1982); U.S. Pat. No. 4,673,641; Ausubel et al., supra; and Sambrook et al., supra).

A number of procedures can be employed when a recombinant BCA-GPCR is being purified. For example, proteins having established molecular adhesion properties can be reversible fused to an BCA-GPCR. With the appropriate ligand, an BCA-GPCR can be selectively adsorbed to a purification column and then freed from the column in a relatively pure form. The fused protein is then removed by enzymatic activity. Finally, an BCA-GPCR could be purified using immunoaffinity columns.

A. Purification of BCA-GPCRs from Recombinant Cells

Recombinant proteins are expressed by transformed bacteria or eukaryotic cells such as CHO cells or insect cells in large amounts, typically after promoter induction; but expression can be constitutive. Promoter induction with IPTG is a one example of an inducible promoter system. Cells are grown according to standard procedures in the art. Fresh or frozen cells are used for isolation of protein.

Proteins expressed in bacteria may form insoluble aggregates ("inclusion bodies"). Several protocols are suitable for purification of BCA-GPCR inclusion bodies. For example, purification of inclusion bodies typically involves the extraction, separation and/or purification of inclusion bodies by disruption of bacterial cells, e.g., by incubation in a buffer of 50 mM TRIS/HCL pH 7.5, 50 mM NaCl, 5 mM $MgCl_2$, 1 mM DTT, 0.1 mM ATP, and 1 mM PMSF. The cell suspension can be lysed using 2–3 passages through a French Press, homogenized using a Polytron (Brinkman Instruments) or sonicated on ice. Alternate methods of lysing bacteria are apparent to those of skill in the art (see, e.g., Sambrook et al., supra; Ausubel et al., supra).

If necessary, the inclusion bodies are solubilized, and the lysed cell suspension is typically centrifuged to remove unwanted insoluble matter. Proteins that formed the inclusion bodies may be renatured by dilution or dialysis with a compatible buffer. Suitable solvents include, but are not limited to urea (from about 4 M to about 8 M), formamide (at least about 80%, volume/volume basis), and guanidine hydrochloride (from about 4 M to about 8 M). Some solvents which are capable of solubilizing aggregate-forming proteins, for example SDS (sodium dodecyl sulfate), 70% formic acid, are inappropriate for use in this procedure due to the possibility of irreversible denaturation of the proteins, accompanied by a lack of immunogenicity and/or activity. Although guanidine hydrochloride and similar agents are denaturants, this denaturation is not irreversible and renaturation may occur upon removal (by dialysis, for example) or dilution of the denaturant, allowing re-formation of immunologically and/or biologically active protein. Other suitable buffers are known to those skilled in the art. The BCA-GPCR is separated from other bacterial proteins by standard separation techniques, e.g., with Ni-NTA agarose resin.

Alternatively, it is possible to purify the BCA-GPCR from bacteria periplasm. After lysis of the bacteria, when the BCA-GPCR is exported into the periplasm of the bacteria, the periplasmic fraction of the bacteria can be isolated by cold osmotic shock in addition to other methods known to skill in the art. To isolate recombinant proteins from the periplasm, the bacterial cells are centrifuged to form a pellet. The pellet is resuspended in a buffer containing 20% sucrose. To lyse the cells, the bacteria are centrifuged and the pellet is resuspended in ice-cold 5 mM $MgSO_4$ and kept in an ice bath for approximately 10 minutes. The cell suspension is centrifuged and the supernatant decanted and saved. The recombinant proteins present in the supernatant can be separated from the host proteins by standard separation techniques well known to those of skill in the art.

B. Standard Protein Separation Techniques for Purifying BCA-GPCRs

Solubility Fractionation

Often as an initial step, particularly if the protein mixture is complex, an initial salt fractionation can separate many of the unwanted host cell proteins (or proteins derived from the cell culture media) from the recombinant protein of interest. The preferred salt is ammonium sulfate. Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol includes adding saturated ammonium sulfate to a protein solution so that the resultant ammonium sulfate concentration is between 20–30%. This concentration will precipitate the most hydrophobic of proteins. The precipitate is then discarded (unless the protein of interest is hydrophobic) and ammonium sulfate is added to the supernatant to a concentration known to precipitate the protein of interest. The precipitate is then solubilized in buffer and the excess salt removed if necessary, either through dialysis or diafiltration. Other methods that rely on solubility of proteins, such as cold ethanol precipitation, are well known to those of skill in the art and can be used to fractionate complex protein mixtures.

Size Differential Filtration

The molecular weight of an BCA-GPCR can be used to isolated it from proteins of greater and lesser size using ultrafiltration through membranes of different pore size (for example, Amicon or Millipore membranes). As a first step, the protein mixture is ultrafiltered through a membrane with a pore size that has a lower molecular weight cut-off than the molecular weight of the protein of interest. The retentate of the ultrafiltration is then ultrafiltered against a membrane with a molecular cut off greater than the molecular weight of the protein of interest. The recombinant protein will pass through the membrane into the filtrate. The filtrate can then be chromatographed as described below.

Column Chromatography

BCA-GPCRs can also be separated from other proteins on the basis of its size, net surface charge, hydrophobicity, and affinity for ligands. In addition, antibodies raised against proteins can be conjugated to column matrices and the proteins immunopurified. All of these methods are well known in the art. It will be apparent to one of skill that chromatographic techniques can be performed at any scale and using equipment from many different manufacturers (e.g., Pharmacia Biotech).

Immunological Detection of BCA-GPCRs

In addition to the detection of BCA-GPCR genes and gene expression using nucleic acid hybridization technology, one can also use immunoassays to detect BCA-GPCRs, e.g., to identify cells such as cancer cells, in particular breast cancer cells, and variants of BCA-GPCRs. Immunoassays can be used to qualitatively or quantitatively analyze BCA-GPCRs. A general overview of the applicable technology can be found in Harlow & Lane, *Antibodies: A Laboratory Manual* (1988).

A. Antibodies to BCA-GPCRs

Methods of producing polyclonal and monoclonal antibodies that react specifically with BCA-GPCRs are known to those of skill in the art (see, e.g., Coligan, *Current Protocols in Immunology* (1991); Harlow & Lane, supra; Goding, *Monoclonal Antibodies: Principles and Practice* (2d ed. 1986); and Kohler & Milstein, *Nature* 256:495–497 (1975). Such techniques include antibody preparation by selection of antibodies from libraries of recombinant antibodies in phage or similar vectors, as well as preparation of polyclonal and monoclonal antibodies by immunizing rabbits or mice (see, e.g., Huse et al., *Science* 246:1275–1281 (1989); Ward et al., *Nature* 341:544–546 (1989)). Such antibodies can be used for therapeutic and diagnostic applications, e.g., in the treatment and/or detection of breast cancer.

A number of BCA-GPCRs comprising immunogens may be used to produce antibodies specifically reactive with BCA-GPCRs. For example, a recombinant BCA-GPCR or an antigenic fragment thereof, is isolated as described herein. Recombinant protein can be expressed in eukaryotic or prokaryotic cells as described above, and purified as generally described above. Recombinant protein is the preferred immunogen for the production of monoclonal or polyclonal antibodies. Alternatively, a synthetic peptide derived from the sequences disclosed herein and conjugated to a carrier protein can be used an immunogen. Naturally occurring protein may also be used either in pure or impure form. The product is then injected into an animal capable of producing antibodies. Either monoclonal or polyclonal antibodies may be generated, for subsequent use in immunoassays to measure the protein.

Methods of production of polyclonal antibodies are known to those of skill in the art. An inbred strain of mice (e.g., BALB/C mice) or rabbits is immunized with the protein using a standard adjuvant, such as Freund's adjuvant, and a standard immunization protocol. The animal's immune response to the immunogen preparation is monitored by taking test bleeds and determining the titer of reactivity to the BCA-GPCR. When appropriately high titers of antibody to the immunogen are obtained, blood is collected from the animal and antisera are prepared. Further fractionation of the antisera to enrich for antibodies reactive to the protein can be done if desired (see Harlow & Lane, supra).

Monoclonal antibodies may be obtained by various techniques familiar to those skilled in the art. Briefly, spleen cells from an animal immunized with a desired antigen are immortalized, commonly by fusion with a myeloma cell (see Kohler & Milstein, *Eur. J. Immunol.* 6:511–519 (1976)). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according to the general protocol outlined by Huse et al., *Science* 246:1275–1281 (1989).

Monoclonal antibodies and polyclonal sera are collected and titered against the immunogen protein in an immunoassay, for example, a solid phase immunoassay with the immunogen immobilized on a solid support. Typically, polyclonal antisera with a titer of $10^4$ or greater are selected and tested for their cross reactivity against non-BCA-GPCR proteins or even other related proteins from other organisms, using a competitive binding immunoassay. Specific polyclonal antisera and monoclonal antibodies will usually bind with a $K_d$ of at least about 0.1 mM, more usually at least about 1 $\mu$M, optionally at least about 0.1 $\mu$M or better, and optionally 0.01 $\mu$M or better.

Once BCA-GPCR specific antibodies are available, BCA-GPCRs can be detected by a variety of immunoassay methods. For a review of immunological and immunoassay procedures, see *Basic and Clinical Immunology* (Stites & Terr eds., 7th ed. 1991). Moreover, the immunoassays of the present invention can be performed in any of several configurations, which are reviewed extensively in *Enzyme Immunoassay* (Maggio, ed., 1980); and Harlow & Lane, supra.

B. Immunological Binding Assays

BCA-GPCRs can be detected and/or quantified using any of a number of well recognized immunological binding assays (see, e.g., U.S. Pat. Nos. 4,366,241; 4,376,110; 4,517,288; and 4,837,168). For a review of the general immunoassays, see also *Methods in Cell Biology: Antibodies in Cell Biology*, volume 37 (Asai, ed. 1993); *Basic and Clinical Immunology* (Stites & Terr, eds., 7th ed. 1991). Immunological binding assays (or immunoassays) typically use an antibody that specifically binds to a protein or antigen of choice (in this case the BCA-GPCR or antigenic subsequence thereof). The antibody (e.g., anti-BCA-GPCR) may be produced by any of a number of means well known to those of skill in the art and as described above.

Immunoassays also often use a labeling agent to specifically bind to and label the complex formed by the antibody and antigen. The labeling agent may itself be one of the moieties comprising the antibody/antigen complex. Thus, the labeling agent may be a labeled BCA-GPCR polypeptide or a labeled anti-BCA-GPCR antibody. Alternatively, the labeling agent may be a third moiety, such a secondary antibody, that specifically binds to the antibody/BCA-GPCR complex (a secondary antibody is typically specific to antibodies of the species from which the first antibody is derived). Other proteins capable of specifically binding immunoglobulin constant regions, such as protein A or protein G may also be used as the label agent. These proteins exhibit a strong non-immunogenic reactivity with immunoglobulin constant regions from a variety of species (see, e.g., Kronval et al., *J. Immunol.* 111:1401–1406 (1973); Akerstrom et al., *J. Immunol.* 135:2589–2542 (1985)). The labeling agent can be modified with a detectable moiety, such as biotin, to which another molecule can specifically bind, such as streptavidin. A variety of detectable moieties are well known to those skilled in the art.

Throughout the assays, incubation and/or washing steps may be required after each combination of reagents. Incubation steps can vary from about 5 seconds to several hours, optionally from about 5 minutes to about 24 hours. However, the incubation time will depend upon the assay format, antigen, volume of solution, concentrations, and the like. Usually, the assays will be carried out at ambient temperature, although they can be conducted over a range of temperatures, such as 10° C. to 40° C.

Non-competitive Assay Formats

Immunoassays for detecting BCA-GPCRs in samples may be either competitive or noncompetitive. Noncompetitive immunoassays are assays in which the amount of antigen is directly measured. In one preferred "sandwich" assay, for example, the anti-BCA-GPCR antibodies can be bound directly to a solid substrate on which they are immobilized. These immobilized antibodies then capture BCA-GPCRs present in the test sample. The BCA-GPCR is thus immobilized is then bound by a labeling agent, such as a second BCA-GPCR antibody bearing a label. Alternatively, the second antibody may lack a label, but it may, in turn, be bound by a labeled third antibody specific to antibodies of the species from which the second antibody is derived. The second or third antibody is typically modified with a detectable moiety, such as biotin, to which another molecule specifically binds, e.g., streptavidin, to provide a detectable moiety.

Competitive Assay Formats

In competitive assays, the amount of BCA-GPCR present in the sample is measured indirectly by measuring the amount of a known, added (exogenous) BCA-GPCR displaced (competed away) from an anti-BCA-GPCR antibody by the unknown BCA-GPCR present in a sample. In one competitive assay, a known amount of BCA-GPCR is added to a sample and the sample is then contacted with an antibody that specifically binds to the BCA-GPCR. The amount of exogenous BCA-GPCR bound to the antibody is inversely proportional to the concentration of BCA-GPCR present in the sample. In a particularly preferred embodiment, the antibody is immobilized on a solid substrate. The amount of BCA-GPCR bound to the antibody may be determined either by measuring the amount of BCA-GPCR present in a BCA-GPCR/antibody complex, or alternatively by measuring the amount of remaining uncomplexed protein. The amount of BCA-GPCR may be detected by providing a labeled BCA-GPCR molecule.

A hapten inhibition assay is another preferred competitive assay. In this assay the known BCA-GPCR, is immobilized on a solid substrate. A known amount of anti-BCA-GPCR antibody is added to the sample, and the sample is then contacted with the immobilized BCA-GPCR. The amount of anti-BCA-GPCR antibody bound to the known immobilized BCA-GPCR is inversely proportional to the amount of BCA-GPCR present in the sample. Again, the amount of immobilized antibody may be detected by detecting either the immobilized fraction of antibody or the fraction of the antibody that remains in solution. Detection may be direct where the antibody is labeled or indirect by the subsequent addition of a labeled moiety that specifically binds to the antibody as described above.

Cross-reactivity Determinations

Immunoassays in the competitive binding format can also be used for crossreactivity determinations. For example, a protein at least partially encoded by SEQ ID NOS:2, 4, 6, or 8 can be immobilized to a solid support. Proteins (e.g., BCA-GPCR proteins and homologs) are added to the assay that compete for binding of the antisera to the immobilized antigen. The ability of the added proteins to compete for binding of the antisera to the immobilized protein is compared to the ability of BCA-GPCRs encoded by SEQ ID NO:2, 4, 6, or 8 to compete with itself. The percent cross-reactivity for the above proteins is calculated, using standard calculations. Those antisera with less than 10% crossreactivity with each of the added proteins listed above are selected and pooled. The cross-reacting antibodies are optionally removed from the pooled antisera by immunoabsorption with the added considered proteins, e.g., distantly related homologs.

The immunoabsorbed and pooled antisera are then used in a competitive binding immunoassay as described above to compare a second protein, thought to be perhaps an allele or polymorphic variant of an BCA-GPCR, to the immunogen protein (i.e., the BCA-GPCR of SEQ ID NOS:2, 4, 6, or 8). In order to make this comparison, the two proteins are each assayed at a wide range of concentrations and the amount of each protein required to inhibit 50% of the binding of the antisera to the immobilized protein is determined. If the amount of the second protein required to inhibit 50% of binding is less than 10 times the amount of the protein encoded by SEQ ID NOS:2, 4, 6, or 8 that is required to inhibit 50% of binding, then the second protein is said to specifically bind to the polyclonal antibodies generated to an BCA-GPCR immunogen.

Other Assay Formats

Western blot (immunoblot) analysis is used to detect and quantify the presence of BCA-GPCR in the sample. The technique generally comprises separating sample proteins by gel electrophoresis on the basis of molecular weight, transferring the separated proteins to a suitable solid support, (such as a nitrocellulose filter, a nylon filter, or derivatized nylon filter), and incubating the sample with the antibodies that specifically bind BCA-GPCR. The anti-BCA-GPCR antibodies specifically bind to the BCA-GPCR on the solid support. These antibodies may be directly labeled or alternatively may be subsequently detected using labeled antibodies (e.g., labeled sheep anti-mouse antibodies) that specifically bind to the anti-BCA-GPCR antibodies.

Other assay formats include liposome immunoassays (LIA), which use liposomes designed to bind specific molecules (e.g., antibodies) and release encapsulated reagents or markers. The released chemicals are then detected according to standard techniques (see Monroe et al., *Amer. Clin. Prod. Rev.* 5:34–41 (1986)).

Reduction of Non-specific Binding

One of skill in the art will appreciate that it is often desirable to minimize non-specific binding in immunoassays. Particularly, where the assay involves an antigen or antibody immobilized on a solid substrate it is desirable to minimize the amount of non-specific binding to the substrate. Means of reducing such non-specific binding are well known to those of skill in the art. Typically, this technique involves coating the substrate with a proteinaceous composition. In particular, protein compositions such as bovine serum albumin (BSA), nonfat powdered milk, and gelatin are widely used with powdered milk being most preferred.

Labels

The particular label or detectable group used in the assay is not a critical aspect of the invention, as long as it does not significantly interfere with the specific binding of the antibody used in the assay. The detectable group can be any material having a detectable physical or chemical property. Such detectable labels have been well-developed in the field of immunoassays and, in general, most any label useful in such methods can be applied to the present invention. Thus, a label is any composition detectable by spectroscopic, photochemical, biochemical, immunochemical, electrical, optical or chemical means. Useful labels in the present invention include magnetic beads (e.g., DYNABEADS™), fluorescent dyes (e.g., fluorescein isothiocyanate, Texas red, rhodamine, and the like), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and colorimetric labels such as colloidal gold or colored glass or plastic beads (e.g., polystyrene, polypropylene, latex, etc.).

The label may be coupled directly or indirectly to the desired component of the assay according to methods well known in the art. As indicated above, a wide variety of labels may be used, with the choice of label depending on sensitivity required, ease of conjugation with the compound, stability requirements, available instrumentation, and disposal provisions.

Non-radioactive labels are often attached by indirect means. Generally, a ligand molecule (e.g., biotin) is covalently bound to the molecule. The ligand then binds to another molecules (e.g., streptavidin) molecule, which is either inherently detectable or covalently bound to a signal system, such as a detectable enzyme, a fluorescent compound, or a chemiluminescent compound. The ligands and their targets can be used in any suitable combination with antibodies that recognize BCA-GPCRs, or secondary antibodies that recognize anti-BCA-GPCR.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidotases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labeling or signal producing systems that may be used, see U.S. Pat. No. 4,391,904.

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product. Finally simple colorimetric labels may be detected simply by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of the target antibodies. In this case, antigen-coated particles are agglutinated by samples comprising the target antibodies. In this format, none of the components need be labeled and the presence of the target antibody is detected by simple visual inspection.

Assays for Modulators of BCA-GPCRs
A. Assays for BCA-GPCR Activity

BCA-GPCRs and their alleles and polymorphic variants are G-protein coupled receptors that participate in signal transduction and are associated with a region amplified in breast cancer cells. The activity of BCA-GPCR polypeptides can be assessed using a variety of in vitro and in vivo assays to determine functional, chemical, and physical effects, e.g., measuring ligand binding (e.g., radioactive ligand binding), second messengers (e.g., cAMP, cGMP, IP$_3$, DAG, or Ca$^{2+}$), ion flux, phosphorylation levels, transcription levels, neurotransmitter levels, and the like. Furthermore, such assays can be used to test for inhibitors and activators of an BCA-GPCR. Modulators can also be genetically altered versions of an BCA-GPCR. Screening assays of the invention are used to identify modulators that can be used as therapeutic co, e.g., antibodies to BCA-GPCRs and antagonists of BCA-GPCR activity.

The BCA-GPCR of the assay will be selected from a polypeptide having a sequence of SEQ ID NOS:2, 4, 6, or 8 or conservatively modified variant thereof. Alternatively, the BCA-GPCR of the assay will be derived from a eukaryote and include an amino acid subsequence having amino acid sequence identity SEQ ID NOS:2, 4, 6, or 8. Generally, the amino acid sequence identity will be at least 70%, optionally at least 85%, optionally at least 90–95%. Optionally, the polypeptide of the assays will comprise a domain of an BCA-GPCR, such as an extracellular domain, transmembrane domain, cytoplasmic domain, ligand binding domain, subunit association domain, active site, and the like. Either an BCA-GPCR or a domain thereof can be covalently linked to a heterologous protein to create a chimeric protein used in the assays described herein.

Modulators of BCA-GPCR activity are tested using BCA-GPCR polypeptides as described above, either recombinant or naturally occurring. The protein can be isolated, expressed in a cell, expressed in a membrane derived from a cell, expressed in tissue or in an animal, either recombinant or naturally occurring. For example, breast cancer cells, normal prostate epithelial cells, placenta, testis tissue, transformed cells, or membranes can be used. Modulation is tested using one of the in vitro or in vivo assays described herein. Signal transduction can also be examined in vitro with soluble or solid state reactions, using a chimeric molecule such as an extracellular domain of a receptor covalently linked to a heterologous signal transduction domain, or a heterologous extracellular domain covalently linked to the transmembrane and or cytoplasmic domain of a receptor. Gene amplification can also be examined. Furthermore, ligand-binding domains of the protein of interest can be used in vitro in soluble or solid state reactions to assay for ligand binding.

Ligand binding to BCA-GPCR, a domain, or chimeric protein can be tested in solution, in a bilayer membrane, attached to a solid phase, in a lipid monolayer, or in vesicles. Binding of a modulator can be tested using, e.g., changes in spectroscopic characteristics (e.g., fluorescence, absorbance, refractive index) hydrodynamic (e.g., shape), chromatographic, or solubility properties.

Receptor-G-protein interactions can also be examined. For example, binding of the G-protein to the receptor or its release from the receptor can be examined. For example, in the absence of GTP, an activator will lead to the formation of a tight complex of a G protein (all three subunits) with the receptor. This complex can be detected in a variety of ways, as noted above. Such an assay can be modified to search for inhibitors. Add an activator to the receptor and G protein in the absence of GTP, form a tight complex, and then screen for inhibitors by looking at dissociation of the receptor-G protein complex. In the presence of GTP, release of the alpha subunit of the G protein from the other two G protein subunits serves as a criterion of activation.

An activated or inhibited G-protein will in turn alter the properties of downstream effectors such as proteins, enzymes, and channels. The classic examples are the activation of cGMP phosphodiesterase by transducin in the visual system, adenylate cyclase by the stimulatory G-protein, phospholipase C by Gq and other cognate G proteins, and modulation of diverse channels by Gi and other G proteins. Downstream consequences can also be examined such as generation of diacyl glycerol and IP3 by phospholipase C, and in turn, for calcium mobilization by IP3.

Activated GPCR receptors become substrates for kinases that phosphorylate the C-terminal tail of the receptor (and possibly other sites as well). Thus, activators will promote the transfer of $^{32}P$ from gamma-labeled GTP to the receptor, which can be assayed with a scintillation counter. The phosphorylation of the C-terminal tail will promote the binding of arrestin-like proteins and will interfere with the binding of G-proteins. The kinase/arrestin pathway plays a key role in the desensitization of many GPCR receptors. For a general review of GPCR signal transduction and methods of assaying signal transduction, see, e.g., *Methods in Enzymology*, vols. 237 and 238 (1994) and volume 96 (1983); Bourne et al., *Nature* 10:349:117–27 (1991); Bourne et al., Nature 348:125–32 (1990); Pitcher et al., *Annu. Rev. Biochem.* 67:653–92 (1998).

Samples or assays that are treated with a potential BCA-GPCR inhibitor or activator are compared to control samples without the test compound, to examine the extent of modulation. Control samples (untreated with activators or inhibitors) are assigned a relative BCA-GPCR activity value of 100. Inhibition of an BCA-GPCR is achieved when the BCA-GPCR activity value relative to the control is about 90%, optionally 50%, optionally 25–0%. Activation of an BCA-GPCR is achieved when the BCA-GPCR activity value relative to the control is 110%, optionally 150%, 200–500%, or 1000–2000%.

Changes in ion flux may be assessed by determining changes in polarization (i.e., electrical potential) of the cell or membrane expressing an BCA-GPCR. One means to determine changes in cellular polarization is by measuring changes in current (thereby measuring changes in polarization) with voltage-clamp and patch-clamp techniques, e.g., the "cell-attached" mode, the "inside-out" mode, and the "whole cell" mode (see, e.g., Ackerman et al., *New Engl. J. Med.* 336:1575–1595 (1997)). Whole cell currents are conveniently determined using the standard methodology (see, e.g., Hamil et al., *PFlugers. Archiv.* 391:85 (1981). Other known assays include: radiolabeled ion flux assays and fluorescence assays using voltage-sensitive dyes (see, e.g., Vestergarrd-Bogind et al., *J. Membrane Biol.* 88:67–75 (1988); Gonzales & Tsien, *Chem. Biol.* 4:269–277 (1997); Daniel et al., *J. Pharmacol. Meth.* 25:185–193 (1991); Holevinsky et al.,*J. Membrane Biology* 137:59–70 (1994)). Generally, the compounds to be tested are present in the range from 1 pM to 100 mM.

The effects of the test compounds upon the function of the polypeptides can be measured by examining any of the parameters described above. Any suitable physiological change that affects GPCR activity can be used to assess the influence of a test compound on the polypeptides of this invention. When the functional consequences are determined using intact cells or animals, one can also measure a variety of effects such as transmitter release, hormone release, transcriptional changes to both known and uncharacterized genetic markers (e.g., northern blots), changes in cell metabolism such as cell growth or pH changes, and changes in intracellular second messengers such as $Ca^{2+}$, IP3 or cAMP.

Preferred assays for G-protein coupled receptors include cells that are loaded with ion or voltage sensitive dyes to report receptor activity. Assays for determining activity of such receptors can also use known agonists and antagonists for other G-protein coupled receptors as negative or positive controls to assess activity of tested compounds. In assays for identifying modulatory compounds (e.g., agonists, antagonists), changes in the level of ions in the cytoplasm or membrane voltage will be monitored using an ion sensitive or membrane voltage fluorescent indicator, respectively. Among the ion-sensitive indicators and voltage probes that may be employed are those disclosed in the Molecular Probes 1997 Catalog. For G-protein coupled receptors, promiscuous G-proteins such as $G\alpha15$ and $G\alpha16$ can be used in the assay of choice (Wilkie et al., *Proc. Nat'l Acad. Sci. USA* 88:10049–10053 (1991)). Such promiscuous G-proteins allow coupling of a wide range of receptors to signal transduction pathways in heterologous cells.

Receptor activation typically initiates subsequent intracellular events, e.g., increases in second messengers such as IP3, which releases intracellular stores of calcium ions. Activation of some G-protein coupled receptors stimulates the formation of inositol triphosphate (IP3) through phospholipase C-mediated hydrolysis of phosphatidylinositol (Berridge & Irvine, Nature 312:315–21 (1984)). IP3 in turn stimulates the release of intracellular calcium ion stores. Thus, a change in cytoplasmic calcium ion levels, or a change in second messenger levels such as IP3 can be used to assess G-protein coupled receptor function. Cells expressing such G-protein coupled receptors may exhibit increased cytoplasmic calcium levels as a result of contribution from both intracellular stores and via activation of ion channels, in which case it may be desirable although not necessary to conduct such assays in calcium-free buffer, optionally supplemented with a chelating agent such as EGTA, to distinguish fluorescence response resulting from calcium release from internal stores.

Other assays can involve determining the activity of receptors which, when activated, result in a change in the level of intracellular cyclic nucleotides, e.g., cAMP or cGMP, by activating or inhibiting downstream effectors such as adenylate cyclase. There are cyclic nucleotide-gated ion channels, e.g., rod photoreceptor cell channels and olfactory neuron channels that are permeable to cations upon activation by binding of cAMP or cGMP (see, e.g., Altenhofen et al., *Proc. Natl Acad. Sci. U.S.A.* 88:9868–9872 (1991) and Dhallan et al., *Nature* 347:184–187 (1990)). In cases where activation of the receptor results in a decrease in cyclic nucleotide levels, it may be preferable to expose the cells to agents that increase intracellular cyclic nucleotide levels, e.g., forskolin, prior to adding a receptor-activating compound to the cells in the assay. Cells for this type of assay can be made by co-transfection of a host cell with DNA encoding a cyclic nucleotide-gated ion channel, GPCR phosphatase and DNA encoding a receptor (e.g., certain glutamate receptors, muscarinic acetylcholine receptors, dopamine receptors, serotonin receptors, and the like), which, when activated, causes a change in cyclic nucleotide levels in the cytoplasm.

In one embodiment, changes in intracellular cAMP or cGMP can be measured using immunoassays. The method described in Offermanns & Simon, *J. Biol. Chem.*

270:15175–15180 (1995) may be used to determine the level of cAMP. Also, the method described in Felley-Bosco et al., *Am. J. Resp. Cell and Mol. Biol.* 11:159–164 (1994) may be used to determine the level of cGMP. Further, an assay kit for measuring cAMP and/or cGMP is described in U.S. Pat. No. 4,115,538, herein incorporated by reference.

In another embodiment, phosphatidyl inositol (PI) hydrolysis can be analyzed according to U.S. Pat. No. 5,436,128, herein incorporated by reference. Briefly, the assay involves labeling of cells with $^3$H-myoinositol for 48 or more hrs. The labeled cells are treated with a test compound for one hour. The treated cells are lysed and extracted in chloroform-methanol-water after which the inositol phosphates were separated by ion exchange chromatography and quantified by scintillation counting. Fold stimulation is determined by calculating the ratio of cpm in the presence of agonist to cpm in the presence of buffer control. Likewise, fold inhibition is determined by calculating the ratio of cpm in the presence of antagonist to cpm in the presence of buffer control (which may or may not contain an agonist).

In another embodiment, transcription levels can be measured to assess the effects of a test compound on signal transduction. A host cell containing the protein of interest is contacted with a test compound for a sufficient time to effect any interactions, and then the level of gene expression is measured. The amount of time to effect such interactions may be empirically determined, such as by running a time course and measuring the level of transcription as a function of time. The amount of transcription may be measured by using any method known to those of skill in the art to be suitable. For example, mRNA expression of the protein of interest may be detected using northern blots or their polypeptide products may be identified using immunoassays. Alternatively, transcription based assays using reporter gene may be used as described in U.S. Pat. No. 5,436,128, herein incorporated by reference. The reporter genes can be, e.g., chloramphenicol acetyltransferase, firefly luciferase, bacterial luciferase, β-galactosidase and alkaline phosphatase. Furthermore, the protein of interest can be used as an indirect reporter via attachment to a second reporter such as green fluorescent protein (see, e.g., Mistili & Spector, *Nature Biotechnology* 15:961–964 (1997)).

The amount of transcription is then compared to the amount of transcription in either the same cell in the absence of the test compound, or it may be compared with the amount of transcription in a substantially identical cell that lacks the protein of interest. A substantially identical cell may be derived from the same cells from which the recombinant cell was prepared but which had not been modified by introduction of heterologous DNA. Any difference in the amount of transcription indicates that the test compound has in some manner altered the activity of the protein of interest.

B. Modulators

The compounds tested as modulators of BCA-GPCRs can be any small chemical compound, or a biological entity, e.g., a macromolecule such as a protein, sugar, nucleic acid or lipid. Alternatively, modulators can be genetically altered versions of an BCA-GPCR. Typically, test compounds will be small chemical molecules and peptides. Essentially any chemical compound can be used as a potential modulator or ligand in the assays of the invention, although most often compounds can be dissolved in aqueous or organic (especially DMSO-based) solutions are used. The assays are designed to screen large chemical libraries by automating the assay steps and providing compounds from any convenient source to assays, which are typically run in parallel (e.g., in microtiter formats on microtiter plates in robotic assays). It will be appreciated that there are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs Switzerland) and the like.

In one preferred embodiment, high throughput screening methods involve providing a combinatorial chemical or peptide library containing a large number of potential therapeutic compounds (potential modulator or ligand compounds). Such "combinatorial chemical libraries" or "ligand libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, *Int. J. Pept. Prot. Res.* 37:487–493 (1991) and Houghton et al., *Nature* 354:84–88 (1991)). Other chemistries for generating chemical diversity libraries can also be used. Such chemistries include, but are not limited to: peptoids (e.g., PCT Publication No. WO 91/19735), encoded peptides (e.g., PCT Publication WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., *Proc. Nat. Acad. Sci. USA* 90:6909–6913 (1993)), vinylogous polypeptides (Hagihara et al., *J. Amer. Chem. Soc.* 114:6568 (1992)), nonpeptidal peptidomimetics with glucose scaffolding (Hirschmann et al., *J. Amer. Chem. Soc.* 114:9217–9218 (1992)), analogous organic syntheses of small compound libraries (Chen et al., *J. Amer. Chem. Soc.* 116:2661 (1994)), oligocarbamates (Cho et al., *Science* 261:1303 (1993)), and/or peptidyl phosphonates (Campbell et al., *J. Org. Chem.* 59:658 (1994)), nucleic acid libraries (see Ausubel, Berger and Sambrook, all supra), peptide nucleic acid libraries (see, e.g., U.S. Pat. No. 5,539,083), antibody libraries (see, e.g., Vaughn et al., *Nature Biotechnology*, 14(3):309–314 (1996) and PCT/US96/10287), carbohydrate libraries (see, e.g., Liang et al., *Science*, 274:1520–1522 (1996) and U.S. Pat. No. 5,593,853), small organic molecule libraries (see, e.g., benzodiazepines, Baum C&EN, January 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Tripos, Inc., St. Louis, Mo., 3D Pharmaceuticals, Exton, Pa., Martek Biosciences, Columbia, Md., etc.).

C. Solid State and Soluble High Throughput Assays

In one embodiment the invention provide soluble assays using molecules such as a domain such as ligand binding domain, an extracellular domain, a transmembrane domain (e.g., one comprising seven transmembrane regions and cytosolic loops), the transmembrane domain and a cytoplasmic domain, an active site, a subunit association region, etc.; a domain that is covalently linked to a heterologous protein to create a chimeric molecule; an BCA-GPCR; or a cell or tissue expressing an BCA-GPCR, either naturally occurring or recombinant. In another embodiment, the invention provides solid phase based in vitro assays in a high throughput format, where the domain, chimeric molecule, BCA-GPCR, or cell or tissue expressing an BCA-GPCR is attached to a solid phase substrate.

In the high throughput assays of the invention, it is possible to screen up to several thousand different modulators or ligands in a single day. In particular, each well of a microtiter plate can be used to run a separate assay against a selected potential modulator, or, if concentration or incubation time effects are to be observed, every 5–10 wells can test a single modulator. Thus, a single standard microtiter plate can assay about 100 (e.g., 96) modulators. If 1536 well plates are used, then a single plate can easily assay from about 100–about 1500 different compounds. It is possible to assay several different plates per day; assay screens for up to about 6,000–20,000 different compounds is possible using the integrated systems of the invention.

The molecule of interest can be bound to the solid state component, directly or indirectly, via covalent or non covalent linkage e.g., via a tag. The tag can be any of a variety of components. In general, a molecule which binds the tag (a tag binder) is fixed to a solid support, and the tagged molecule of interest (e.g., the signal transduction molecule of interest) is attached to the solid support by interaction of the tag and the tag binder.

A number of tags and tag binders can be used, based upon known molecular interactions well described in the literature. For example, where a tag has a natural binder, for example, biotin, protein A, or protein G, it can be used in conjunction with appropriate tag binders (avidin, streptavidin, neutravidin, the Fc region of an immunoglobulin, etc.) Antibodies to molecules with natural binders such as biotin are also widely available and appropriate tag binders; see, SIGMA Immunochemicals 1998 catalogue SIGMA, St. Louis Mo.).

Similarly, any haptenic or antigenic compound can be used in combination with an appropriate antibody to form a tag/tag binder pair. Thousands of specific antibodies are commercially available and many additional antibodies are described in the literature. For example, in one common configuration, the tag is a first antibody and the tag binder is a second antibody which recognizes the first antibody. In addition to antibody-antigen interactions, receptor-ligand interactions are also appropriate as tag and tag-binder pairs. For example, agonists and antagonists of cell membrane receptors (e.g., cell receptor-ligand interactions such as transferrin, c-kit, viral receptor ligands, cytokine receptors, chemokine receptors, interleukin receptors, immunoglobulin receptors and antibodies, the cadherein family, the integrin family, the selectin family, and the like; see, e.g., Pigott & Power, *The Adhesion Molecule Facts Book I* (1993).

Similarly, toxins and venoms, viral epitopes, hormones (e.g., opiates, steroids, etc.), intracellular receptors (e.g. which mediate the effects of various small ligands, including steroids, thyroid hormone, retinoids and vitamin D; peptides), drugs, lectins, sugars, nucleic acids (both linear and cyclic polymer configurations), oligosaccharides, proteins, phospholipids and antibodies can all interact with various cell receptors.

Synthetic polymers, such as polyurethanes, polyesters, polycarbonates, polyureas, polyamides, polyethyleneimines, polyarylene sulfides, polysiloxanes, polyimides, and polyacetates can also form an appropriate tag or tag binder. Many other tag/tag binder pairs are also useful in assay systems described herein, as would be apparent to one of skill upon review of this disclosure.

Common linkers such as peptides, polyethers, and the like can also serve as tags, and include polypeptide sequences, such as poly gly sequences of between about 5 and 200 amino acids. Such flexible linkers are known to persons of skill in the art. For example, poly(ethelyne glycol) linkers are available from Shearwater Polymers, Inc. Huntsville, Ala. These linkers optionally have amide linkages, sulfhydryl linkages, or heterofunctional linkages.

Tag binders are fixed to solid substrates using any of a variety of methods currently available. Solid substrates are commonly derivatized or functionalized by exposing all or a portion of the substrate to a chemical reagent which fixes a chemical group to the surface which is reactive with a portion of the tag binder. For example, groups which are suitable for attachment to a longer chain portion would include amines, hydroxyl, thiol, and carboxyl groups. Aminoalkylsilanes and hydroxyalkylsilanes can be used to functionalize a variety of surfaces, such as glass surfaces. The construction of such solid phase biopolymer arrays is well described in the literature. See, e.g., Merrifield, *J. Am. Chem. Soc.* 85:2149–2154 (1963) (describing solid phase synthesis of, e.g., peptides); Geysen et al., *J. Immun. Meth.* 102:259–274 (1987) (describing synthesis of solid phase components on pins); Frank & Doring, *Tetrahedron* 44:60316040 (1988) (describing synthesis of various peptide sequences on cellulose disks); Fodor et al., *Science*, 251:767–777 (1991); Sheldon et al., *Clinical Chemistry* 39(4):718–719 (1993); and Kozal et al., *Nature Medicine* 2(7):753759 (1996) (all describing arrays of biopolymers fixed to solid substrates). Non-chemical approaches for fixing tag binders to substrates include other common methods, such as heat, cross-linking by UV radiation, and the like.

D. Computer-based Assays

Yet another assay for compounds that modulate BCA-GPCR activity involves computer assisted drug design, in which a computer system is used to generate a three-dimensional structure of BCA-GPCR based on the structural information encoded by the amino acid sequence. The input amino acid sequence interacts directly and actively with a preestablished algorithm in a computer program to yield secondary, tertiary, and quaternary structural models of the protein. The models of the protein structure are then examined to identify regions of the structure that have the ability to bind, e.g., ligands. These regions are then used to identify ligands that bind to the protein.

The three-dimensional structural model of the protein is generated by entering protein amino acid sequences of at least 10 amino acid residues or corresponding nucleic acid sequences encoding an BCA-GPCR polypeptide into the computer system. The amino acid sequence of the polypeptide or the nucleic acid encoding the polypeptide is selected from the group consisting of SEQ ID NOS:1–8 and conservatively modified versions thereof. The amino acid sequence represents the primary sequence or subsequence of the protein, which encodes the structural information of the protein. At least 10 residues of the amino acid sequence (or a nucleotide sequence encoding 10 amino acids) are entered into the computer system from computer keyboards, computer readable substrates that include, but are not limited to, electronic storage media (e.g., magnetic diskettes, tapes, cartridges, and chips), optical media (e.g., CD ROM), information distributed by internet sites, and by RAM. The three-dimensional structural model of the protein is then generated by the interaction of the amino acid sequence and the computer system, using software known to those of skill in the art.

The amino acid sequence represents a primary structure that encodes the information necessary to form the secondary, tertiary and quaternary structure of the protein of interest. The software looks at certain parameters encoded by the primary sequence to generate the structural model. These parameters are referred to as "energy terms," and primarily include electrostatic potentials, hydrophobic potentials, solvent accessible surfaces, and hydrogen bonding. Secondary energy terms include van der Waals potentials. Biological molecules form the structures that minimize the energy terms in a cumulative fashion. The computer program is therefore using these terms encoded by the primary structure or amino acid sequence to create the secondary structural model.

The tertiary structure of the protein encoded by the secondary structure is then formed on the basis of the energy terms of the secondary structure. The user at this point can enter additional variables such as whether the protein is membrane bound or soluble, its location in the body, and its cellular location, e.g., cytoplasmic, surface, or nuclear. These variables along with the energy terms of the secondary structure are used to form the model of the tertiary structure. In modeling the tertiary structure, the computer program matches hydrophobic faces of secondary structure with like, and hydrophilic faces of secondary structure with like.

Once the structure has been generated, potential ligand binding regions are identified by the computer system. Three-dimensional structures for potential ligands are generated by entering amino acid or nucleotide sequences or chemical formulas of compounds, as described above. The three-dimensional structure of the potential ligand is then compared to that of the BCA-GPCR protein to identify ligands that bind to BCA-GPCR. Binding affinity between the protein and ligands is determined using energy terms to determine which ligands have an enhanced probability of binding to the protein.

Computer systems are also used to screen for mutations, polymorphic variants, alleles and interspecies homologs of BCA-GPCR genes. Such mutations can be associated with disease states or genetic traits. As described above, Gene-Chip™ and related technology can also be used to screen for mutations, polymorphic variants, alleles and interspecies homologs. Once the variants are identified, diagnostic assays can be used to identify patients having such mutated genes. Identification of the mutated BCA-GPCR genes involves receiving input of a first nucleic acid or amino acid sequence encoding an BCA-GPCR, selected from the group consisting of SEQ ID NOS:1–8 and conservatively modified versions thereof. The sequence is entered into the computer system as described above. The first nucleic acid or amino acid sequence is then compared to a second nucleic acid or amino acid sequence that has substantial identity to the first sequence. The second sequence is entered into the computer system in the manner described above. Once the first and second sequences are compared, nucleotide or amino acid differences between the sequences are identified. Such sequences can represent allelic differences in BCA-GPCR genes, and mutations associated with disease states and genetic traits.

Kits

BCA-GPCRs and their homologs are a useful tool for identifying cells such as cancer cells, for forensics and paternity determinations, for diagnosing diseases such as cancer, e.g., breast cancer, and for examining signal transduction. BCA-GPCR specific reagents that specifically hybridize to BCA-GPCR nucleic acids, such as BCA-GPCR probes and primers, and BCA-GPCR specific reagents that specifically bind to an BCA-GPCR protein, e.g., BCA-GPCR antibodies are used to examine signal transduction regulation.

Nucleic acid assays for the presence of BCA-GPCR DNA and RNA in a sample include numerous techniques are known to those skilled in the art, such as Southern analysis, northern analysis, dot blots, RNase protection, S1 analysis, amplification techniques such as PCR and LCR, and in situ hybridization. In in situ hybridization, for example, the target nucleic acid is liberated from its cellular surroundings in such as to be available for hybridization within the cell while preserving the cellular morphology for subsequent interpretation and analysis (see Example 1). The following articles provide an overview of the art of in situ hybridization: Singer et al., *Biotechniques* 4:230–250 (1986); Haase et al., *Methods in Virology*, vol. VII, pp. 189–226 (1984); and *Nucleic Acid Hybridization: A Practical Approach* (Hames et al, eds. 1987). In addition, BCA-GPCR protein can be detected with the various immunoassay techniques described above. The test sample is typically compared to both a positive control (e.g., a sample expressing a recombinant BCA-GPCR) and a negative control.

The present invention also provides for kits for screening for modulators of BCA-GPCRs. Such kits can be prepared from readily available materials and reagents. For example, such kits can comprise any one or more of the following materials: an BCA-GPCR, reaction tubes, and instructions for testing BCA-GPCR activity. Optionally, the kit contains biologically active BCA-GPCR. A wide variety of kits and components can be prepared according to the present invention, depending upon the intended user of the kit and the particular needs of the user.

Administration and Pharmaceutical Compositions

BCA-GPCR modulators can be administered directly to the mammalian subject for modulation of signal transduction in vivo, e.g., for the treatment of a cancer such as breast cancer. Administration is by any of the routes normally used for introducing a modulator compound into ultimate contact with the tissue to be treated. The BCA-GPCR modulators are administered in any suitable manner, optionally with pharmaceutically acceptable carriers. Suitable methods of administering such modulators are available and well known to those of skill in the art, and, although more than one route can be used to administer a particular composition, a particular route can often provide a more immediate and more effective reaction than another route.

Pharmaceutically acceptable carriers are determined in part by the particular composition being administered, as well as by the particular method used to administer the composition. Accordingly, there is a wide variety of suitable formulations of pharmaceutical compositions of the present invention (see, e.g., *Remington's Pharmaceutical Sciences*, 17$^{th}$ ed. 1985)).

The BCA-GPCR modulators, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for administration include aqueous and non-aqueous solutions, isotonic sterile solutions, which can contain antioxidants, buffers, bacteriostats, and solutes that render the formulation isotonic, and aqueous and non-aqueous sterile suspensions that can include suspending agents, solubilizers, thickening agents, stabilizers, and preservatives. In the practice of this invention, compositions can be administered, for example, by orally, topically, intravenously, intraperitoneally, intravesically or intrathecally. Optionally, the compositions are administered orally or nasally. The formulations of compounds can be presented in unit-dose or multi-dose sealed containers, such as ampules and vials. Solutions and suspensions can be prepared from sterile powders, granules, and tablets of the kind previously described. The modulators can also be administered as part a of prepared food or drug.

The dose administered to a patient, in the context of the present invention should be sufficient to effect a beneficial response in the subject over time. Such doses are administered prophylactically or to an individual already suffering from the disease. The compositions are administered to a patient in an amount sufficient to elicit an effective protective or therapeutic response in the patient. An amount adequate to accomplish this is defined as "therapeutically effective dose." The dose will be determined by the efficacy of the particular BCA-GPCR modulators (e.g., GPCR antagonists and anti-GPCR antibodies) employed and the condition of the subject, as well as the body weight or surface area of the area to be treated. The size of the dose also will be determined by the existence, nature, and extent of any adverse side-effects that accompany the administration of a particular compound or vector in a particular subject.

In determining the effective amount of the modulator to be administered in a physician may evaluate circulating plasma levels of the modulator, modulator toxicities, and the production of anti-modulator antibodies. In general, the dose equivalent of a modulator is from about 1 ng/kg to 10 mg/kg for a typical subject.

For administration, BCA-GPCR modulators of the present invention can be administered at a rate determined by the LD-50 of the modulator, and the side-effects of the inhibitor at various concentrations, as applied to the mass and overall health of the subject. Administration can be accomplished via single or divided doses.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

EXAMPLES

The following examples are provided by way of illustration only and not by way of limitation. Those of skill in the art will readily recognize a variety of noncritical parameters that could be changed or modified to yield essentially similar results.

Example I

Identification and Cloning of Novel BCA-GPCRs

Four human BCA-GPCRs were cloned and their nucleic acid sequences are provided in SEQ ID NO:1, 3, 5, and 7. The deduced amino acid sequences are provided in SEQ ID NO:2, 4, 6, and 8. The novel BCA-GPCRs were designated BCA-GPCR-1, -2, -3, and -4, respectively.

These sequences can be amplified from cDNA or genomic DNA with standard PCR conditions using the following PCR primers:

ATGTTGGGGAACGTCGCCATC (SEQ ID NO:9) and
TCATCCACAGAGCCTCCAGAT (SEQ ID NO:10) (BCA-GPCR-1)
ATGGGAAAGGACAATCCAGTT (SEQ ID NO:11) and
CTAAGAGAGTAACTCCAGCAA (SEQ ID NO:12); (BCA-GPCR-2)
ATGGAAATAGCCAATGTGAGTTC (SEQ ID NO:13) and
TAAATTTGCGCCAGCTTGCCTG (SEQ ID NO:14);) BCA-GPCR-3) and
ATGGTGAGACATACCAATGAGAG (SEQ ID NO:15) and
CATAAAATATTTACTCCCAGAGCC (SEQ ID NO:16) (BCA-GPCR-4).

Example II mRNA Expression and Gene Amplification of BCA-GPCR-3 in Breast Cancer Cells and Tumors Gene amplification of BCA-GPCR-3 in breast cancer cell lines and tumors was measured according to standard methodology (see FIG. 1).

BCA-GPCR-3 mRNA expression in breast cancer cell lines was examined using RT-PCR, according to standard methodology (see FIGS. 2 and 3). BCA-GPCR-3 mRNA levels were elevated in cancer cell lines from both amplified and non-amplified tumors, a hallmark of oncogenes.

What is claimed is:

1. An isolated polypeptide comprising the amino acid sequence of SEQ ID NO:6.

2. An isolated polypeptide consisting of the amino acid sequence of SEQ ID NO:6.

3. An isolated polypeptide comprising at least 200 contiguous amino acids of SEQ ID NO:6.

4. An isolated polypeptide comprising the 319 amino acid region of SEQ ID NO:6 from the methionine residue at position 22 through the isoleucine residue at position 340.

* * * * *

SEQUENCE LISTING

<160> NUMBER OF SEQ ID NOS: 16

<210> SEQ ID NO 1
<211> LENGTH: 1035
<212> TYPE: DNA
<213> ORGANISM: Homo sapiens
<220> FEATURE:
<221> NAME/KEY: CDS
<222> LOCATION: (42)..(974)
<223> OTHER INFORMATION: human breast cancer amplified G-protein coupled receptor 1 (BCA-GPCR-1)

<400> SEQUENCE: 1

```
agtgccagaa aatgccgcaa catgaaaagt gacaaccata g ctc tta ggg gac tcc          56
                                              Leu Leu Gly Asp Ser
                                                1               5 cct aaa gcc ttc atc ctt ctg ggt gtg tct gac agg ccg tgg ctg gaa           104
Pro Lys Ala Phe Ile Leu Leu Gly Val Ser Asp Arg Pro Trp Leu Glu
            10                  15                  20 ctc cct ctc ttt gtg gtc ctc ctg ctg tcc tat gtg ctg gcc atg ttg          152
Leu Pro Leu Phe Val Val Leu Leu Leu Ser Tyr Val Leu Ala Met Leu
        25                  30                  35 ggg aac gtc gcc atc atc ctg gca tcc cgg gtg gat cct caa ctc cac          200
Gly Asn Val Ala Ile Ile Leu Ala Ser Arg Val Asp Pro Gln Leu His
    40                  45                  50 agc ccc atg tac atc ttc ctc agt cac ctg tcc ttc ctg gac ctc tgc          248
Ser Pro Met Tyr Ile Phe Leu Ser His Leu Ser Phe Leu Asp Leu Cys
55                  60                  65 tac acc acc acg aca gtc cct cag atg ctg gtc aac atg ggc agt tcc          296
Tyr Thr Thr Thr Thr Val Pro Gln Met Leu Val Asn Met Gly Ser Ser
 70                  75                  80                  85 cag aag acc atc agc tat gga ggc tgc act gtg caa tat gca gtc ttc          344
Gln Lys Thr Ile Ser Tyr Gly Gly Cys Thr Val Gln Tyr Ala Val Phe
                90                  95                 100 cac tgg ctg gga tgc acg gag tgc atc gtc ctg gcc gcc atg gcc ctg          392
His Trp Leu Gly Cys Thr Glu Cys Ile Val Leu Ala Ala Met Ala Leu
            105                 110                 115 gac cgc tac gtg gcc agc tgc aag ccc ctg cac tat gcc gtt ctc atg          440
Asp Arg Tyr Val Ala Ser Cys Lys Pro Leu His Tyr Ala Val Leu Met
        120                 125                 130 cac cgt gct ctc tgt cag cag ctc gtg gct ctg gcc tgg ctc agt ggc          488
His Arg Ala Leu Cys Gln Gln Leu Val Ala Leu Ala Trp Leu Ser Gly
    135                 140                 145 ttc ggc aac tcc ttc gtg cag gtg gtc ctg acg gtg caa ttg cca ttc          536
Phe Gly Asn Ser Phe Val Gln Val Val Leu Thr Val Gln Leu Pro Phe
150                 155                 160                 165 tgc ggg cgg cag gtg ctg aac aac ttt ttc tgt gag gtg ccg gcc gtg          584
Cys Gly Arg Gln Val Leu Asn Asn Phe Phe Cys Glu Val Pro Ala Val
                170                 175                 180 atc aag ctg tcg tgt gct gac acc gct atg aat gac acc ata ctg gct          632
Ile Lys Leu Ser Cys Ala Asp Thr Ala Met Asn Asp Thr Ile Leu Ala
            185                 190                 195 gtg ctg gtg gcc ttc ttc gtg ttg gtg ccc ctg gct ctc atc ctt ctc          680
Val Leu Val Ala Phe Phe Val Leu Val Pro Leu Ala Leu Ile Leu Leu
        200                 205                 210 tcc tat ggc ttt att gcc cgg gca gtg ctc agg atc cag tcc tcc aag          728
Ser Tyr Gly Phe Ile Ala Arg Ala Val Leu Arg Ile Gln Ser Ser Lys
    215                 220                 225 gga cga cac aag gcc ttt ggg acg tgt tcc tcc cac ctg atg atc gtc          776
Gly Arg His Lys Ala Phe Gly Thr Cys Ser Ser His Leu Met Ile Val
```

```
                230                 235                 240                 245
tcc ctc ttc tac cta cct gcg att tac atg tat ctg cag ccc cct tcc           824
Ser Leu Phe Tyr Leu Pro Ala Ile Tyr Met Tyr Leu Gln Pro Pro Ser
                250                 255                 260 agc tac tcc caa gag cag ggc aaa ttt att tct ctc ttc tat tcc ata           872
Ser Tyr Ser Gln Glu Gln Gly Lys Phe Ile Ser Leu Phe Tyr Ser Ile
            265                 270                 275 atc acc ccc act ctc aat ccc ttc acc tac acc ctg aga aat aaa gat           920
Ile Thr Pro Thr Leu Asn Pro Phe Thr Tyr Thr Leu Arg Asn Lys Asp
            280                 285                 290 atg aag ggg gct ctg agg aga ctt ctg gcc agg atc tgg agg ctc tgt           968
Met Lys Gly Ala Leu Arg Arg Leu Leu Ala Arg Ile Trp Arg Leu Cys
            295                 300                 305 gga tga tgaggacatg agatgtagca tctccatcaa ttaaagaaca cagcacaagt          1024
Gly
310 ctattgtgca c                                                             1035
```

<210> SEQ ID NO 2
<211> LENGTH: 310
<212> TYPE: PRT
<213> ORGANISM: Homo sapiens

<400> SEQUENCE: 2

```
Leu Leu Gly Asp Ser Pro Lys Ala Phe Ile Leu Leu Gly Val Ser Asp
 1               5                  10                  15

Arg Pro Trp Leu Glu Leu Pro Leu Phe Val Val Leu Leu Leu Ser Tyr
                20                  25                  30

Val Leu Ala Met Leu Gly Asn Val Ala Ile Ile Leu Ala Ser Arg Val
            35                  40                  45

Asp Pro Gln Leu His Ser Pro Met Tyr Ile Phe Leu Ser His Leu Ser
        50                  55                  60

Phe Leu Asp Leu Cys Tyr Thr Thr Thr Thr Val Pro Gln Met Leu Val
 65                  70                  75                  80

Asn Met Gly Ser Ser Gln Lys Thr Ile Ser Tyr Gly Gly Cys Thr Val
                85                  90                  95

Gln Tyr Ala Val Phe His Trp Leu Gly Cys Thr Glu Cys Ile Val Leu
            100                 105                 110

Ala Ala Met Ala Leu Asp Arg Tyr Val Ala Ser Cys Lys Pro Leu His
        115                 120                 125

Tyr Ala Val Leu Met His Arg Ala Leu Cys Gln Gln Leu Val Ala Leu
    130                 135                 140

Ala Trp Leu Ser Gly Phe Gly Asn Ser Phe Val Gln Val Val Leu Thr
145                 150                 155                 160

Val Gln Leu Pro Phe Cys Gly Arg Gln Val Leu Asn Asn Phe Phe Cys
                165                 170                 175

Glu Val Pro Ala Val Ile Lys Leu Ser Cys Ala Asp Thr Ala Met Asn
            180                 185                 190

Asp Thr Ile Leu Ala Val Leu Ala Phe Phe Val Leu Val Pro Leu
        195                 200                 205

Ala Leu Ile Leu Leu Ser Tyr Gly Phe Ile Ala Arg Ala Val Leu Arg
    210                 215                 220

Ile Gln Ser Ser Lys Gly Arg His Lys Ala Phe Gly Thr Cys Ser Ser
225                 230                 235                 240

His Leu Met Ile Val Ser Leu Phe Tyr Leu Pro Ala Ile Tyr Met Tyr
                245                 250                 255
```

```
Leu Gln Pro Pro Ser Ser Tyr Ser Gln Glu Gln Gly Lys Phe Ile Ser
        260                 265                 270

Leu Phe Tyr Ser Ile Ile Thr Pro Thr Leu Asn Pro Phe Thr Tyr Thr
    275                 280                 285

Leu Arg Asn Lys Asp Met Lys Gly Ala Leu Arg Arg Leu Leu Ala Arg
    290                 295                 300

Ile Trp Arg Leu Cys Gly
305                 310

<210> SEQ ID NO 3
<211> LENGTH: 1411
<212> TYPE: DNA
<213> ORGANISM: Homo sapiens
<220> FEATURE:
<221> NAME/KEY: CDS
<222> LOCATION: (118)..(1113)
<223> OTHER INFORMATION: human breast cancer amplified G-protein coupled
      receptor 2 (BCA-GPCR-2)

<400> SEQUENCE: 3
ggcaaatggc tctcttaact tcacagacct gtaaatggaa attggagagt gccagatcat    60
ctgcatgtgc ccccttatct aattctttgg ttgtttctct gtaatagctg gtggatt     117 atg gga aag gac aat gcc agt tac cta cag gca ttc atc ctg gtg ggc    165
Met Gly Lys Asp Asn Ala Ser Tyr Leu Gln Ala Phe Ile Leu Val Gly
  1               5                  10                  15 tct tct gat cgg cct gga ctg gag aaa att ctc ttt gct gtt atc ttg    213
Ser Ser Asp Arg Pro Gly Leu Glu Lys Ile Leu Phe Ala Val Ile Leu
             20                  25                  30 atc ttc tgc atc ctg acc ctg gtg ggc aac act gcc atc atc ctc ttg    261
Ile Phe Cys Ile Leu Thr Leu Val Gly Asn Thr Ala Ile Ile Leu Leu
         35                  40                  45 ctg gtc atg gat gtc agg ctc cac aca ccc atg tac ttc ttt ctt ggg    309
Leu Val Met Asp Val Arg Leu His Thr Pro Met Tyr Phe Phe Leu Gly
     50                  55                  60 aat ctg tct ttc tta gat ctc tgc ttt aca gca agc att gcc cct cag    357
Asn Leu Ser Phe Leu Asp Leu Cys Phe Thr Ala Ser Ile Ala Pro Gln
 65                  70                  75                  80 ctg ctg tgg aac ctg ggg ggt cca gag aag acc atc acc tac cac ggc    405
Leu Leu Trp Asn Leu Gly Gly Pro Glu Lys Thr Ile Thr Tyr His Gly
                 85                  90                  95 tgt gtg gcc caa ctc tac atc tac atg atg ctg ggc tcc acc gag tgc    453
Cys Val Ala Gln Leu Tyr Ile Tyr Met Met Leu Gly Ser Thr Glu Cys
            100                 105                 110 gtc ctc ctg gtt gtc atg tcc cat gac cgc tat gtg gcc gtc tgc cgg    501
Val Leu Leu Val Val Met Ser His Asp Arg Tyr Val Ala Val Cys Arg
        115                 120                 125 tcc ctg cac tac atg gca gtc atg cgc cca cat ctc tgc ctg cag ctg    549
Ser Leu His Tyr Met Ala Val Met Arg Pro His Leu Cys Leu Gln Leu
    130                 135                 140 gtg act gtg gcc tgg tgc tgt ggc ttc cta aac tcc ttc atc atg tgt    597
Val Thr Val Ala Trp Cys Cys Gly Phe Leu Asn Ser Phe Ile Met Cys
145                 150                 155                 160 cct cag acg atg cag ctc tcc cgg tgt gga cgt cgc agg gtg gac cac    645
Pro Gln Thr Met Gln Leu Ser Arg Cys Gly Arg Arg Arg Val Asp His
                165                 170                 175 ttc ctg tgt gag atg cct gct ctt att gcc atg tct tgt gag gaa acc    693
Phe Leu Cys Glu Met Pro Ala Leu Ile Ala Met Ser Cys Glu Glu Thr
            180                 185                 190 atg ctg gta gaa gcg att cac ctt tgc cct ggg ggt ggc tct cct cct    741
```

-continued

```
Met Leu Val Glu Ala Ile His Leu Cys Pro Gly Gly Ser Pro Pro
            195                 200                 205 ggt gcc gct ctc cct cat cct cat ctc tat ggc gtg att gca gcc gcg      789
Gly Ala Ala Leu Pro His Pro His Leu Tyr Gly Val Ile Ala Ala Ala
    210                 215                 220 gtg ctg agg atg aag tca gca gca ggg cga aag aaa gcc ttc cac acc      837
Val Leu Arg Met Lys Ser Ala Ala Gly Arg Lys Lys Ala Phe His Thr
225                 230                 235                 240 tgc tct tct cac ctc aca gtg gtc tct ctc ttc tac gga acc atc atc      885
Cys Ser Ser His Leu Thr Val Val Ser Leu Phe Tyr Gly Thr Ile Ile
                245                 250                 255 tac gtg tac ctg aag ccg gcc aac agc tac tcc caa gat cag ggg aag      933
Tyr Val Tyr Leu Lys Pro Ala Asn Ser Tyr Ser Gln Asp Gln Gly Lys
            260                 265                 270 ttc ctg act ctc ttc tac acc atc gtc att ccc agc atc aac ccc ctc      981
Phe Leu Thr Leu Phe Tyr Thr Ile Val Ile Pro Ser Ile Asn Pro Leu
        275                 280                 285 atc tac act ttg agg aac aag gat gtg aag ggg acc atg aag aaa ctt      1029
Ile Tyr Thr Leu Arg Asn Lys Asp Val Lys Gly Thr Met Lys Lys Leu
    290                 295                 300 ctg ggg tgg gag aaa ggg gct ggg gag cct caa cga ggg gaa cac tct      1077
Leu Gly Trp Glu Lys Gly Ala Gly Glu Pro Gln Arg Gly Glu His Ser
305                 310                 315                 320 agt aat gta gac agt ttg ctg gag tta ctc tct tag atgtgtctgt           1123
Ser Asn Val Asp Ser Leu Leu Glu Leu Leu Ser
                325                 330 ggccatgtgg agaactaata ttcaaggagt agagtgaacg cgggtgggaa aatgctttcg    1183
agtttgaccc cgtcctctgc cctctggatg tgaagtggtt tccttctgtt tgaagttgcc    1243
tgcttcagga tatctctgct gtatcttgca ctttccttgt cttttttgatt tatccacaac   1303 tgctggggac ttacaaaact aattcaatca cccaaaggca ctgggcagtc tgcagattat    1363
gtcatggatg tcaaataaaa attgagacaa catgaaaaaa aaaaaaaa                 1411

<210> SEQ ID NO 4
<211> LENGTH: 331
<212> TYPE: PRT
<213> ORGANISM: Homo sapiens

<400> SEQUENCE: 4

Met Gly Lys Asp Asn Ala Ser Tyr Leu Gln Ala Phe Ile Leu Val Gly
  1               5                  10                  15

Ser Ser Asp Arg Pro Gly Leu Glu Lys Ile Leu Phe Ala Val Ile Leu
                20                  25                  30

Ile Phe Cys Ile Leu Thr Leu Val Gly Asn Thr Ala Ile Ile Leu Leu
            35                  40                  45

Leu Val Met Asp Val Arg Leu His Thr Pro Met Tyr Phe Phe Leu Gly
        50                  55                  60

Asn Leu Ser Phe Leu Asp Leu Cys Phe Thr Ala Ser Ile Ala Pro Gln
65                  70                  75                  80

Leu Leu Trp Asn Leu Gly Gly Pro Glu Lys Thr Ile Thr Tyr His Gly
                85                  90                  95

Cys Val Ala Gln Leu Tyr Ile Tyr Met Met Leu Gly Ser Thr Glu Cys
            100                 105                 110

Val Leu Leu Val Val Met Ser His Asp Arg Tyr Val Ala Val Cys Arg
        115                 120                 125

Ser Leu His Tyr Met Ala Val Met Arg Pro His Leu Cys Leu Gln Leu
    130                 135                 140
```

```
Val Thr Val Ala Trp Cys Cys Gly Phe Leu Asn Ser Phe Ile Met Cys
145                 150                 155                 160

Pro Gln Thr Met Gln Leu Ser Arg Cys Gly Arg Arg Val Asp His
                165                 170                 175

Phe Leu Cys Glu Met Pro Ala Leu Ile Ala Met Ser Cys Glu Glu Thr
            180                 185                 190

Met Leu Val Glu Ala Ile His Leu Cys Pro Gly Gly Ser Pro Pro
        195                 200                 205

Gly Ala Ala Leu Pro His Pro His Leu Tyr Gly Val Ile Ala Ala Ala
    210                 215                 220

Val Leu Arg Met Lys Ser Ala Ala Gly Arg Lys Lys Ala Phe His Thr
225                 230                 235                 240

Cys Ser Ser His Leu Thr Val Val Ser Leu Phe Tyr Gly Thr Ile Ile
                245                 250                 255

Tyr Val Tyr Leu Lys Pro Ala Asn Ser Tyr Ser Gln Asp Gln Gly Lys
                260                 265                 270

Phe Leu Thr Leu Phe Tyr Thr Ile Val Ile Pro Ser Ile Asn Pro Leu
                275                 280                 285

Ile Tyr Thr Leu Arg Asn Lys Asp Val Lys Gly Thr Met Lys Lys Leu
        290                 295                 300

Leu Gly Trp Glu Lys Gly Ala Gly Glu Pro Gln Arg Gly Glu His Ser
305                 310                 315                 320

Ser Asn Val Asp Ser Leu Leu Glu Leu Leu Ser
                325                 330

<210> SEQ ID NO 5
<211> LENGTH: 1351
<212> TYPE: DNA
<213> ORGANISM: Homo sapiens
<220> FEATURE:
<221> NAME/KEY: CDS
<222> LOCATION: (86)..(1108)
<223> OTHER INFORMATION: human breast cancer amplified G-protein coupled
      receptor 3 (BCA-GPCR-3)

<400> SEQUENCE: 5
gattgtgtct ctaaaaaaga ataacataaa atgaactaaa atacactttt aatgtttgct      60
aactgatgta attgcttcat gtctc atg ccc tgt atg ccc tgt gct ctt ccc       112
                            Met Pro Cys Met Pro Cys Ala Leu Pro
                              1               5 aca ggt ggc ctt ttg ccc cac ccc cag cat aca atg atg gaa ata gcc      160
Thr Gly Gly Leu Leu Pro His Pro Gln His Thr Met Met Glu Ile Ala
 10                  15                  20                  25 aat gtg agt tct cca gaa gtc ttt gtc ctc ctg ggc ttc tcc gca cga      208
Asn Val Ser Ser Pro Glu Val Phe Val Leu Leu Gly Phe Ser Ala Arg
                 30                  35                  40 ccc tca cta gaa act gtc ctc ttc ata gtt gtc ttg agt ttt tac atg      256
Pro Ser Leu Glu Thr Val Leu Phe Ile Val Val Leu Ser Phe Tyr Met
             45                  50                  55 gta tcg atc ttg ggc aat ggc atc atc att ctg gtc tcc cat aca gat      304
Val Ser Ile Leu Gly Asn Gly Ile Ile Ile Leu Val Ser His Thr Asp
         60                  65                  70 gtg cac ctc cac aca cct atg tac ttc ttt ctt gcc aac ctc tcc ttc      352
Val His Leu His Thr Pro Met Tyr Phe Phe Leu Ala Asn Leu Ser Phe
     75                  80                  85 ctg gac atg agc ttc acc acg agc att gtc cca cag ctc ctg gct aac      400
Leu Asp Met Ser Phe Thr Thr Ser Ile Val Pro Gln Leu Leu Ala Asn
 90                  95                 100                 105
```

```
ctc tgg gga cca cag aaa acc ata agc tat gga ggg tgt gtg gtc cag        448
Leu Trp Gly Pro Gln Lys Thr Ile Ser Tyr Gly Gly Cys Val Val Gln
            110                 115                 120 ttc tat atc tcc cat tgg ctg ggg gca acc gag tgt gtc ctg ctg gcc        496
Phe Tyr Ile Ser His Trp Leu Gly Ala Thr Glu Cys Val Leu Leu Ala
    125                 130                 135 acc atg tcc tat gac cgc tac gct gcc atc tgc agg cca ctc cat tac        544
Thr Met Ser Tyr Asp Arg Tyr Ala Ala Ile Cys Arg Pro Leu His Tyr
        140                 145                 150 act gtc att atg cat cca cag ctt tgc ctt ggg cta gct ttg gcc tcc        592
Thr Val Ile Met His Pro Gln Leu Cys Leu Gly Leu Ala Leu Ala Ser
155                 160                 165 tgg ctg ggg ggt ctg acc acc agc atg gtg ggc tcc acg ctc acc atg        640
Trp Leu Gly Gly Leu Thr Thr Ser Met Val Gly Ser Thr Leu Thr Met
170                 175                 180                 185 ctc cta ccg ctg tgt ggg aac aat tgc atc gac cac ttc ttt tgc gag        688
Leu Leu Pro Leu Cys Gly Asn Asn Cys Ile Asp His Phe Phe Cys Glu
                190                 195                 200 atg ccc ctc att atg caa ctg gct tgt gtg gat acc agc ctc aat gag        736
Met Pro Leu Ile Met Gln Leu Ala Cys Val Asp Thr Ser Leu Asn Glu
        205                 210                 215 atg gag atg tac ctg gcc agc ttt gtc ttt gtt gtc ctg cct ctg ggg        784
Met Glu Met Tyr Leu Ala Ser Phe Val Phe Val Val Leu Pro Leu Gly
        220                 225                 230 ctc atc ctg gtc tct tac ggc cac att gcc cgg gcc gtg ttg aag atc        832
Leu Ile Leu Val Ser Tyr Gly His Ile Ala Arg Ala Val Leu Lys Ile
        235                 240                 245 agg tca gca gaa ggg cgg aga aag gca ttc aac acc tgt tct tcc cac        880
Arg Ser Ala Glu Gly Arg Arg Lys Ala Phe Asn Thr Cys Ser Ser His
250                 255                 260                 265 gtg gct gtg gtg tct ctg ttt tac ggg agc atc atc ttc atg tat ctc        928
Val Ala Val Val Ser Leu Phe Tyr Gly Ser Ile Ile Phe Met Tyr Leu
                270                 275                 280 cag cca gcc aag agc acc tcc cat gag cag ggc aag ttc ata gct ctg        976
Gln Pro Ala Lys Ser Thr Ser His Glu Gln Gly Lys Phe Ile Ala Leu
        285                 290                 295 ttc tac acc gta gtc act cct gcg ttg aac cca ctt att tac acc ctg       1024
Phe Tyr Thr Val Val Thr Pro Ala Leu Asn Pro Leu Ile Tyr Thr Leu
        300                 305                 310 agg aac acg gag gtg aag agc gcc ctc cgg cac atg gta tta gag aac       1072
Arg Asn Thr Glu Val Lys Ser Ala Leu Arg His Met Val Leu Glu Asn
315                 320                 325 tgc tgt ggc tct gca ggc aag ctg gcg caa att tag agactccagt            1118
Cys Cys Gly Ser Ala Gly Lys Leu Ala Gln Ile
330                 335                 340 gccttctgag aaggaagatc aagtttacat cgagcaaagt gaccttggaa gacagggcac    1178
ttgggatgtc gttttctct  taatattgtt tgagctcaag gtagatggaa atctgaaagg    1238
agtgtgctca tgccatttcc agaccaagaa aacacattta ttatttgcta attatcatag    1298
ttttgttcaa ttgcgttgtt ggttttttgct atatatacac atgttgactg tca           1351

<210> SEQ ID NO 6
<211> LENGTH: 340
<212> TYPE: PRT
<213> ORGANISM: Homo sapiens

<400> SEQUENCE: 6

Met Pro Cys Met Pro Cys Ala Leu Pro Thr Gly Gly Leu Leu Pro His
1               5                   10                  15
```

```
Pro Gln His Thr Met Met Glu Ile Ala Asn Val Ser Ser Pro Glu Val
         20                  25                  30

Phe Val Leu Leu Gly Phe Ser Ala Arg Pro Ser Leu Glu Thr Val Leu
         35                  40                  45

Phe Ile Val Val Leu Ser Phe Tyr Met Val Ser Ile Leu Gly Asn Gly
     50                  55                  60

Ile Ile Ile Leu Val Ser His Thr Asp Val His Leu His Thr Pro Met
 65                  70                  75                  80

Tyr Phe Phe Leu Ala Asn Leu Ser Phe Leu Asp Met Ser Phe Thr Thr
                 85                  90                  95

Ser Ile Val Pro Gln Leu Leu Ala Asn Leu Trp Gly Pro Gln Lys Thr
             100                 105                 110

Ile Ser Tyr Gly Gly Cys Val Val Gln Phe Tyr Ile Ser His Trp Leu
         115                 120                 125

Gly Ala Thr Glu Cys Val Leu Leu Ala Thr Met Ser Tyr Asp Arg Tyr
     130                 135                 140

Ala Ala Ile Cys Arg Pro Leu His Tyr Thr Val Ile Met His Pro Gln
145                 150                 155                 160

Leu Cys Leu Gly Leu Ala Leu Ala Ser Trp Leu Gly Leu Thr Thr
                 165                 170                 175

Ser Met Val Gly Ser Thr Leu Thr Met Leu Leu Pro Leu Cys Gly Asn
             180                 185                 190

Asn Cys Ile Asp His Phe Phe Cys Glu Met Pro Leu Ile Met Gln Leu
         195                 200                 205

Ala Cys Val Asp Thr Ser Leu Asn Glu Met Glu Met Tyr Leu Ala Ser
     210                 215                 220

Phe Val Phe Val Val Leu Pro Leu Gly Leu Ile Leu Val Ser Tyr Gly
225                 230                 235                 240

His Ile Ala Arg Ala Val Leu Lys Ile Arg Ser Ala Glu Gly Arg Arg
                 245                 250                 255

Lys Ala Phe Asn Thr Cys Ser Ser His Val Ala Val Val Ser Leu Phe
             260                 265                 270

Tyr Gly Ser Ile Ile Phe Met Tyr Leu Gln Pro Ala Lys Ser Thr Ser
         275                 280                 285

His Glu Gln Gly Lys Phe Ile Ala Leu Phe Tyr Thr Val Val Thr Pro
     290                 295                 300

Ala Leu Asn Pro Leu Ile Tyr Thr Leu Arg Asn Thr Glu Val Lys Ser
305                 310                 315                 320

Ala Leu Arg His Met Val Leu Glu Asn Cys Cys Gly Ser Ala Gly Lys
                 325                 330                 335

Leu Ala Gln Ile
             340

<210> SEQ ID NO 7
<211> LENGTH: 1065
<212> TYPE: DNA
<213> ORGANISM: Homo sapiens
<220> FEATURE:
<221> NAME/KEY: CDS
<222> LOCATION: (26)..(1030)
<223> OTHER INFORMATION: human breast cancer amplified G-protein coupled
      receptor 4 (BCA-GPCR-4)

<400> SEQUENCE: 7
attgtcactc atttaaccct atgtg atg tgt tat ctt tct cag cta tgc ctc      52
                            Met Cys Tyr Leu Ser Gln Leu Cys Leu
```

| | | | | | | | | | | | | | | | | |
|---|---|---|---|---|---|---|---|---|---|---|---|---|---|---|---|---|
| | | | | 1 | | | | 5 | | | | | | | | |
| agc | ctt | ggg | gaa | cac | act | tta | cat | atg | ggg | atg | gtg | aga | cat | acc | aat | 100 |
| Ser | Leu | Gly | Glu | His | Thr | Leu | His | Met | Gly | Met | Val | Arg | His | Thr | Asn | |
| 10 | | | | 15 | | | | 20 | | | | | | 25 | | |
| gag | agc | aac | cta | gca | ggt | ttc | atc | ctt | tta | ggg | ttt | tct | gat | tat | gct | 148 |
| Glu | Ser | Asn | Leu | Ala | Gly | Phe | Ile | Leu | Leu | Gly | Phe | Ser | Asp | Tyr | Ala | |
| | | | 30 | | | | | 35 | | | | | 40 | | | |
| cag | tta | cag | aag | gtt | cta | ttt | gtg | ctc | ata | ttg | att | ctg | tat | tta | cta | 196 |
| Gln | Leu | Gln | Lys | Val | Leu | Phe | Val | Leu | Ile | Leu | Ile | Leu | Tyr | Leu | Leu | |
| | | | 45 | | | | | 50 | | | | | 55 | | | |
| act | att | ttg | ggg | aat | acc | acc | atc | att | ctg | gtt | tct | cgt | ctg | gaa | ccc | 244 |
| Thr | Ile | Leu | Gly | Asn | Thr | Thr | Ile | Ile | Leu | Val | Ser | Arg | Leu | Glu | Pro | |
| | | | 60 | | | | 65 | | | | | 70 | | | | |
| aag | ctt | cat | atg | ccg | atg | tat | ttc | ttc | ctt | tct | cat | ctc | tcc | ttc | ctg | 292 |
| Lys | Leu | His | Met | Pro | Met | Tyr | Phe | Phe | Leu | Ser | His | Leu | Ser | Phe | Leu | |
| | 75 | | | | | 80 | | | | | 85 | | | | | |
| tac | cgc | tgc | ttc | acc | agc | agt | gtt | att | ccc | cag | ctc | ctg | gta | aac | ctg | 340 |
| Tyr | Arg | Cys | Phe | Thr | Ser | Ser | Val | Ile | Pro | Gln | Leu | Leu | Val | Asn | Leu | |
| 90 | | | | | 95 | | | | | 100 | | | | | 105 | |
| tgg | gaa | ccc | atg | aaa | act | atc | gcc | tat | ggt | ggc | tgt | ttg | gtt | cac | ctt | 388 |
| Trp | Glu | Pro | Met | Lys | Thr | Ile | Ala | Tyr | Gly | Gly | Cys | Leu | Val | His | Leu | |
| | | | | 110 | | | | | 115 | | | | | 120 | | |
| tac | aac | tcc | cat | gcc | ctg | gga | tcc | act | gag | tgc | gtc | ctc | ccg | gct | ctg | 436 |
| Tyr | Asn | Ser | His | Ala | Leu | Gly | Ser | Thr | Glu | Cys | Val | Leu | Pro | Ala | Leu | |
| | | | 125 | | | | | 130 | | | | | 135 | | | |
| atg | tcc | tgt | gac | cgc | tat | gtg | gct | gtc | tgc | cgt | cct | ctc | cat | tac | act | 484 |
| Met | Ser | Cys | Asp | Arg | Tyr | Val | Ala | Val | Cys | Arg | Pro | Leu | His | Tyr | Thr | |
| | | 140 | | | | | 145 | | | | | 150 | | | | |
| gtc | tta | atg | cat | atc | cat | ctc | tgc | atg | gcc | ttg | gca | tct | atg | gca | tgg | 532 |
| Val | Leu | Met | His | Ile | His | Leu | Cys | Met | Ala | Leu | Ala | Ser | Met | Ala | Trp | |
| 155 | | | | | 160 | | | | | 165 | | | | | | |
| ctc | agt | gga | ata | gcc | acc | acc | ctg | gta | cag | tcc | acc | ctc | acc | ctg | cag | 580 |
| Leu | Ser | Gly | Ile | Ala | Thr | Thr | Leu | Val | Gln | Ser | Thr | Leu | Thr | Leu | Gln | |
| 170 | | | | | 175 | | | | | 180 | | | | | 185 | |
| ctg | ccc | ttc | tgt | ggg | cat | cgc | caa | gtg | gat | cat | ttc | atc | tgc | gag | gtc | 628 |
| Leu | Pro | Phe | Cys | Gly | His | Arg | Gln | Val | Asp | His | Phe | Ile | Cys | Glu | Val | |
| | | | | 190 | | | | | 195 | | | | | 200 | | |
| cct | gtg | ctc | atc | aag | ctg | gct | tgt | gtg | ggc | acc | acg | ttt | aac | gag | gct | 676 |
| Pro | Val | Leu | Ile | Lys | Leu | Ala | Cys | Val | Gly | Thr | Thr | Phe | Asn | Glu | Ala | |
| | | | 205 | | | | | 210 | | | | | 215 | | | |
| gag | ctt | ttt | gtg | gct | agt | atc | ctt | ttc | ctt | ata | gtg | cct | gtc | tca | ttc | 724 |
| Glu | Leu | Phe | Val | Ala | Ser | Ile | Leu | Phe | Leu | Ile | Val | Pro | Val | Ser | Phe | |
| | | 220 | | | | | 225 | | | | | 230 | | | | |
| atc | ctg | gtc | tcc | tct | ggc | tac | att | gcc | cac | gca | gtg | ttg | agg | att | aag | 772 |
| Ile | Leu | Val | Ser | Ser | Gly | Tyr | Ile | Ala | His | Ala | Val | Leu | Arg | Ile | Lys | |
| | 235 | | | | | 240 | | | | | 245 | | | | | |
| tca | gct | acc | ggg | aga | cag | aaa | gca | ttt | ggg | acc | tgc | ttc | tcc | cac | ctg | 820 |
| Ser | Ala | Thr | Gly | Arg | Gln | Lys | Ala | Phe | Gly | Thr | Cys | Phe | Ser | His | Leu | |
| 250 | | | | | 255 | | | | | 260 | | | | | 265 | |
| aca | gtg | gtc | acc | atc | ttt | tat | gga | acc | atc | atc | ttc | atg | tat | ctg | cag | 868 |
| Thr | Val | Val | Thr | Ile | Phe | Tyr | Gly | Thr | Ile | Ile | Phe | Met | Tyr | Leu | Gln | |
| | | | | 270 | | | | | 275 | | | | | 280 | | |
| cca | gcc | aag | agt | aga | tcc | agg | gac | cag | ggc | aag | ttt | gtt | tct | ctc | ttc | 916 |
| Pro | Ala | Lys | Ser | Arg | Ser | Arg | Asp | Gln | Gly | Lys | Phe | Val | Ser | Leu | Phe | |
| | | | 285 | | | | | 290 | | | | | 295 | | | |
| tac | act | gtg | gta | acc | cgc | atg | ctt | aac | cct | ctt | att | tat | acc | ttg | agg | 964 |
| Tyr | Thr | Val | Val | Thr | Arg | Met | Leu | Asn | Pro | Leu | Ile | Tyr | Thr | Leu | Arg | |
| | | 300 | | | | | 305 | | | | | 310 | | | | |
| atc | aag | gag | gtg | aaa | ggg | gca | tta | aag | aaa | gtt | cta | gca | aag | gct | ctg | 1012 |

```
Ile Lys Glu Val Lys Gly Ala Leu Lys Lys Val Leu Ala Lys Ala Leu
    315                 320                 325 gga gta aat att tta tga ttattaaaaa aaaatttaag tgacactgtg atgaa        1065
Gly Val Asn Ile Leu
330                 335
```

<210> SEQ ID NO 8
<211> LENGTH: 334
<212> TYPE: PRT
<213> ORGANISM: Homo sapiens

<400> SEQUENCE: 8

```
Met Cys Tyr Leu Ser Gln Leu Cys Leu Ser Leu Gly Glu His Thr Leu
  1               5                  10                  15

His Met Gly Met Val Arg His Thr Asn Glu Ser Asn Leu Ala Gly Phe
             20                  25                  30

Ile Leu Leu Gly Phe Ser Asp Tyr Ala Gln Leu Gln Lys Val Leu Phe
         35                  40                  45

Val Leu Ile Leu Ile Leu Tyr Leu Leu Thr Ile Leu Gly Asn Thr Thr
 50                  55                  60

Ile Ile Leu Val Ser Arg Leu Glu Pro Lys Leu His Met Pro Met Tyr
 65                  70                  75                  80

Phe Phe Leu Ser His Leu Ser Phe Leu Tyr Arg Cys Phe Thr Ser Ser
                 85                  90                  95

Val Ile Pro Gln Leu Leu Val Asn Leu Trp Glu Pro Met Lys Thr Ile
            100                 105                 110

Ala Tyr Gly Gly Cys Leu Val His Leu Tyr Asn Ser His Ala Leu Gly
        115                 120                 125

Ser Thr Glu Cys Val Leu Pro Ala Leu Met Ser Cys Asp Arg Tyr Val
    130                 135                 140

Ala Val Cys Arg Pro Leu His Tyr Thr Val Leu Met His Ile His Leu
145                 150                 155                 160

Cys Met Ala Leu Ala Ser Met Ala Trp Leu Ser Gly Ile Ala Thr Thr
                165                 170                 175

Leu Val Gln Ser Thr Leu Thr Leu Gln Leu Pro Phe Cys Gly His Arg
            180                 185                 190

Gln Val Asp His Phe Ile Cys Glu Val Pro Val Leu Ile Lys Leu Ala
        195                 200                 205

Cys Val Gly Thr Thr Phe Asn Glu Ala Glu Leu Phe Val Ala Ser Ile
    210                 215                 220

Leu Phe Leu Ile Val Pro Val Ser Phe Ile Leu Val Ser Ser Gly Tyr
225                 230                 235                 240

Ile Ala His Ala Val Leu Arg Ile Lys Ser Ala Thr Gly Arg Gln Lys
                245                 250                 255

Ala Phe Gly Thr Cys Phe Ser His Leu Thr Val Val Thr Ile Phe Tyr
            260                 265                 270

Gly Thr Ile Ile Phe Met Tyr Leu Gln Pro Ala Lys Ser Arg Ser Arg
        275                 280                 285

Asp Gln Gly Lys Phe Val Ser Leu Phe Tyr Thr Val Thr Arg Met
    290                 295                 300

Leu Asn Pro Leu Ile Tyr Thr Leu Arg Ile Lys Glu Val Lys Gly Ala
305                 310                 315                 320

Leu Lys Lys Val Leu Ala Lys Ala Leu Gly Val Asn Ile Leu
                325                 330
```

```
<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence:PCR
      amplification primer for BCA-GPCR-1

<400> SEQUENCE: 9
atgttgggga acgtcgccat c                                           21

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence:PCR
      amplification primer for BCA-GPCR-1

<400> SEQUENCE: 10
tcatccacag agcctccaga t                                           21

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence:PCR
      amplification primer for BCA-GPCR-2

<400> SEQUENCE: 11
atgggaaagg acaatccagt t                                           21

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence:PCR
      amplification primer for BCA-GPCR-2

<400> SEQUENCE: 12
ctaagagagt aactccagca a                                           21

<210> SEQ ID NO 13
<211> LENGTH: 23
<212> TYPE: DNA
<213> ORGANISM: Artificial Sequence
<220> FEATURE:
<223> OTHER INFORMATION: Description of Artificial Sequence:PCR
      amplification primer for BCA-GPCR-3

<400> SEQUENCE: 13
atggaaatag ccaatgtgag ttc                                         23

<210> SEQ ID NO 14
<211> LENGTH: 22
<212> TYPE: DNA
<213> ORGANISM: Artificial Sequence
<220> FEATURE:
<223> OTHER INFORMATION: Description of Artificial Sequence:PCR
      amplification primer for BCA-GPCR-3

<400> SEQUENCE: 14
taaatttgcg ccagcttgcc tg                                          22

<210> SEQ ID NO 15
```

```
<211> LENGTH: 23
<212> TYPE: DNA
<213> ORGANISM: Artificial Sequence
<220> FEATURE:
<223> OTHER INFORMATION: Description of Artificial Sequence:PCR
      amplification primer for BCA-GPCR-4

<400> SEQUENCE: 15
atggtgagac ataccaatga gag                                          23

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence:PCR
      amplification primer for BCA-GPCR-4

<400> SEQUENCE: 16
cataaaatat ttactcccag agcc                                         24
```